(12) United States Patent
Hilton

(10) Patent No.: US 7,476,732 B2
(45) Date of Patent: *Jan. 13, 2009

(54) NUCLEIC ACID ENCODING α CHAIN OF HUMAN IL-11 RECEPTOR

(75) Inventor: Douglas James Hilton, Warrandyte (AU)

(73) Assignee: The Walter and Eliza Hall Institute of Medical Research (AU)

(*) Notice: Subject to any disclaimer, the term of this patent is extended or adjusted under 35 U.S.C. 154(b) by 0 days.

This patent is subject to a terminal disclaimer.

(21) Appl. No.: 11/204,563

(22) Filed: Aug. 16, 2005

(65) Prior Publication Data

US 2006/0051842 A1    Mar. 9, 2006

Related U.S. Application Data

(60) Continuation of application No. 09/532,263, filed on Mar. 22, 2000, now Pat. No. 7,002,000, which is a division of application No. 08/702,665, filed on Dec. 20, 1996, now Pat. No. 6,274,708.

(51) Int. Cl.
    *C12N 15/12*    (2006.01)
    *C12N 15/63*    (2006.01)

(52) U.S. Cl. .................................. 536/23.5; 435/320.1

(58) Field of Classification Search ........................ None
See application file for complete search history.

(56) References Cited

U.S. PATENT DOCUMENTS 7,002,000 B1 * 2/2006 Hilton ........................ 536/23.5

FOREIGN PATENT DOCUMENTS

| WO | WO 91/18982 | 12/1991 |
| WO | WO 93/18047 | 9/1993 |
| WO | WO 96/19574 | 6/1996 |

OTHER PUBLICATIONS

Gorman et al., "Cloning and Expession of a Gene Encoding an Interleukin 3 Receptor-Like Protein: Identification of Another Member of the Cytokine Receptor Gene Family", *Proc. Natl. Acad. Sci. USA*, 87:5459-5463 (1990).
Hilton et al., "Cloning of a Murine IL-11 Receptor α-Chain: Requirement for gp130 for High Affinity Binding and Signal Transduction", *The EMBO Journal*, 13(20):4765-4775 (1994).
Itoh et al., "Cloning of an Interleukin-3 Receptor Gene: A Member of a Distinct Receptor Gene Family", *Science*, 247:324-327 (1990).
Tashiro et al., "Signal Sequence Trap: A Cloning Strategy for Secreted Proteins and Type I Membrane Proteins", *Science*, 261:600-601 (1993).
Gorman DM et al., "Chomosomal Localization and Organization of the Murine Genes Encoding the Beta Subunits (AIC2A and AIC2B) of the Interleukin 3, Granulocyte/Macrophage Colony Stimulating Factor, and Interleukin 5", *J. Biol. Chem.*, 267:15842-15848 (1993).
Reiger et al., "Glossary of Genetics and Cytogenetics", *Springer-Verlag, 4th edition*, 16-19 (1996).
Born et al., "Indentification and Characterization of Two Novel Emembers of a Novel Class of the Interleukin-1 Receptor (IL-1R) Family", *J. Biol Chem.*, 275:29946-29954 (2000).

* cited by examiner

*Primary Examiner*—Prema Mertz
(74) *Attorney, Agent, or Firm*—Scully, Scott, Murphy & Presser, P.C.

(57) ABSTRACT

The present invention relates generally to novel haemopoietin receptors, or components or parts thereof and to a method for cloning genetic sequences encoding same. More particularly, the subject invention is directed to recombinant or synthetic haemopoietin receptors or components or parts thereof. The receptor molecules or components or parts thereof and their genetic sequences of the present invention are useful in the development of a wide range agonists, antagonists and therapeutics and diagnostic reagents based on ligand interaction with its receptor.

3 Claims, 19 Drawing Sheets

Figure 1:
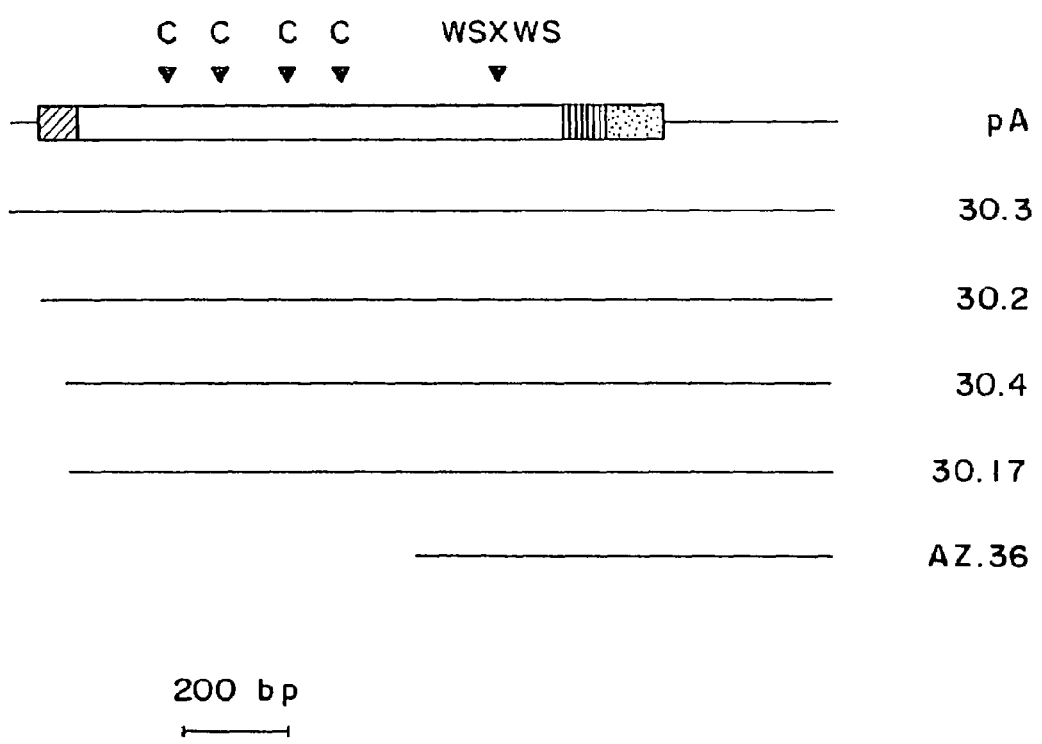

```
                       MSSSCSGLTRVLVAVATALVSSS--SPCPQAWGPPVQYGQPGRPVMLCCPG-VSAGTP
                       MLTVGCTLLVALLAAPAVALVLGS---CRALEVANGTVTSLPGATVTLICPGKEAAGN
IG-LIKE                MAAPVPWACCAVLAAAA----VVYAQRHSPQEAPHVQYERLGSDVTLPCGTANWDAA
                       MCHQQLVISWESLVFLASPLVAIWELKKDVYVVELDWYPDAPGEMVLTCDTPEEDG-
                       MTSSHAMNITPLAQLALLFSTLLIPGTQ--ALLAPT-TPDA-GSALNLTFDPWTRT--

M NR1
           M IL-6R
           H CNTFR
           H IL-12p40
           M GM-CSFR

-VDWFRDGDSRLLQG------    PDSGLGHRLVLAQVDSPCEGTXVCQTLDGVSGGMVT-
                       VTIHWVYSGSQNR-------     EWTTGNTLVLRDVQLSDTGDXLCSLNDHLVGTVPLL
                       --VTWRVNGTDLA-------     PDLLNGSQLVLHGLELGHSGLXACFHRDSWHLRHQVL
                       --ITWTLDQSSEV-------     LGSGKTLTIQVKEFGDAGQXTCHKGGEVLSHSLLL
                       --LTWACDTAAGNVTVTSCTVTSREAGIHRRVSPFGCRCWFRRMMALHHGVTLDVNGT

M NR1
           M IL-6R
           H CNTFR
           H IL-12p40
           M GM-CSFR

LKLGF--------
                       VDV----------
                       LHVGL--------
                       LHKKEDGIWSTDILKDQKE
                       VGGAAAHWRLS-FVNESAA

M NR1
           M IL-6R
           H CNTFR
           H IL-12p40
           M GM-CSFR
```

FIG. 2A

```
M NR1       PPARPEVSCQAVDX-EMFSCTWSPGQVSGLPTRYLTSYRKKTLPGAESQRESPSTGPWP
M IL-6R     PPEEPKLSCFRKNPLVMAICEWRPSSTPSPTTKAVLFAKKINTTNGK------SDFQVP
H CNTFR     PPREPVLSCRSNTXPKGFYCSWHLPTPTYIPNTFNVTVLH-----------GSKIMV
H IL-12p40  PKNKTFLRCEAKNYSGRFTCWWLTTI----STDLTFSVKSSRGSS--------DPQGVT
M GM-CSFR   GSGAENLTCEIRAA-RFLSCAWREGPAA--PADVRYSLRVLNST---------GHDVAR

M NR1       CPQDPLE------------------ASRCVVHG-----AELWSEYRTNVTEVNPL--GASTCLLD
M IL-6R     CQYSQQLK-----------------SFSCQVE------ILEGDKVYHIVSLCVANSVGSKSSHNE
H CNTFR     CEKDPAL------------------KNRCHIRYMHLFSTIKYKVSISVSNAL---GHNATAIT
H IL-12p40  CGAATLSAERVRGDNKEYEYSVECQEDSACPAAKESLPIEVMVDAV--HKLKYENYTSS
M GM-CSFR   CMADPGDDV----------------ITQCIA------NDLSLLGSEAYLVVTGRSGAGPVRFLDD

M NR1       VRLQSTLR---
M IL-6R     AFHSLKMVQ--
H CNTFR     FDEFTIVK---
H IL-12p40  FFIRDIIK---
M GM-CSFR   VVATKALERLG
```

FIG.2B

SD100B

```
M NR1      PDPPQGLRVESVPGYPRRLHGSWTYPASWPRQPHFL-----LKLRLQXRPAQHPAWSTV
M IL-6R    PDPPANLVVSAIPGRPRWLKVSWQHPETWDPSY-YL-----LQFQLRXRPVWSKEFTVL
H CNTFR    PDPPENVVARPVPSNPRRLEVTWQTPSTWPDPESFPLKFF-LRYRPLILDQWQHVELSD
H IL12p40  PDPPNNLQLK-PLKNSRQVEVSWEXPDTWSTPHSYFSLTFCVQVQGKSKREKKDRVFTD
M GM-CSFR  --PPRDVT---ASCNSSHCTVSWAPPSTWASLTARDFQFE-VQWQSAEPGSTPRKVLVV

M NR1      RPIGL--EEVITDAVAGLPMAVRVSARDFLDAGTWSAWSPEAWGTPSTG-PLQDEIPD-
M IL-6R    LLPVAQYQCVIHDALRGVKMVQVRGKEELDLGQWSEWSPEVTGTPWIAEPRTTPAGIL
H CNTFR    GT-----AHTITDAYAGKEYIIQVAAKDNEI-GTWSDWSVAAHATPWTEEPRHLTTEAQ
H IL12p40  KT-------SATVICRKNASISVRAQDRYYSSSWSEWASVPCS*
M GM-CSFR  KETRL----AFPSPAHGGMKVKVRAGDTRMK-HWGEWSPAHPL-EAEDTRVP------

M NR1      WSQGHGQQLEVVAQEDSPAPARPSLQPDPRPLDHRDPLEQ
M IL-6R    WNPTQVSVEDSANHEDQYESSTEATSVLAPVQESSSMSLPT
H CNTFR    AAETTSTTSSLAPPPTTKIC---------------------
M GM-CSF   -----------------------------------------

TM/CYT

M NR1      VAVLASLLGIFSCLGLAVGALALGLWLRLRRSGKDGPQKPGLLA--PMIPVEKLPGIPN
M IL-6R    FLVAGGSLAFGLLLCVFIIL------RLKQKWKSEAEKESKTTSPPPPYSLGPLKPT
H CNTFR    DPGELGSGGGPSAPFLVSVPITLALAAAATASSLLI*
M GM-CSF   ALLYAVTACAVLLCALALGVTC-----RRFEVTRR----------LYPPIPGIRD

M NR1      LQRTPENFS*
M IL-6R    FLIVPLLTPHSSGSDNTVNHSCLGVRDAQSPYDNSNRDYLFPR*
M GM-CSF   KVSDDVRVNPETLRKDLLQP*
```

FIG.2C

```
TCTAACAGCC TTACCCCACT TGGTGCATCA ATTTTCTCC TAGGAAGCCT CAGTTTTGGA          60

GAGGAAGAGC CAGGCTTTAG CTCCCATCTC AGGGGTCGGG GATTTTTGAC TCTACCCTC        120

CCCACAG ATG AGC AGC TGC TCA GGG CTG TCA AGC GTC CTG GTG GCC            169
        Met Ser Ser Cys Ser Gly Leu Ser Arg Val Leu Val Ala
        1                5                    10

GTG GCT ACA GCC CTG GTG TCT GCC TCC CCC TGC CCC CAG GCC TGG            217
Val Ala Thr Ala Leu Val Ser Ala Ser Pro Cys Pro Gln Ala Trp
 15                  20                  25                  30

GGC CCC CCA GGG GTC CAG TAT GGG CAG CCA GGG GTG AGG TCC GTG AAG CTG    265
Gly Pro Pro Gly Val Gln Tyr Gly Gln Pro Gly Val Arg Ser Val Lys Leu
            35                  40                  45

TGT TGT CCT GGA GTG ACT GCC GGG GAC CCA GTG TCC TGG TTT CGG GAT        313
Cys Cys Pro Gly Val Thr Ala Gly Asp Pro Val Ser Trp Phe Arg Asp
         50                  55                  60

GGG GAG CCA AAG CTG CTC CAG GGA CCT GAC TCT GGG CTA GGC CAT GAA        361
Gly Glu Pro Lys Leu Leu Gln Gly Pro Asp Ser Gly Leu Gly His Glu
 65                  70                  75

CTG GTC CTG GCC CAG GCA GAC AGC ACT GAT GAG GGC ACC TAC ATC TGC        409
Leu Val Leu Ala Gln Ala Asp Ser Thr Asp Glu Gly Thr Tyr Ile Cys
         80                  85                  90

CAG ACC CTG GAT GGT GCA CTT GGG GCA GAC GTG GGC ACA CTG CAG CTG GGC    457
Gln Thr Leu Asp Gly Ala Leu Gly Ala Asp Val Gly Thr Leu Gln Leu Gly
 95                 100                 105                 110
```

FIG. 8A

```
TAC CCT CCA GCC CGC CCT GTT TCC TGC CAA GCA GCC GAC TAT GAG      505
Tyr Pro Pro Ala Arg Pro Val Ser Cys Gln Ala Ala Asp Tyr Glu
            115                 120                 125

AAC TTC TCT TGC ACT TGG AGT CCC AGC ATC AGC GGT TTA CCC ACC      553
Asn Phe Ser Cys Thr Trp Ser Pro Ser Ile Ser Gly Leu Pro Thr
            130                 135                 140

CGC TAC CTC ACC TCC TAC AGG AAG ACA GTC CTA GGA GCT GAT AGC      601
Arg Tyr Leu Thr Ser Tyr Arg Lys Thr Val Leu Gly Ala Asp Ser
            145                 150                 155

CAG AGG AGT CCA TCC ACA GGG CCC TGG CCA TGC CAG GAT CCC          649
Gln Arg Ser Pro Ser Thr Gly Pro Trp Pro Cys Gln Asp Pro
            160                 165             170

CTA GGG GCT GCC CGC TGT GTT GTC CAC GGG GCT GAG TTC TGG AGC CAG  697
Leu Gly Ala Ala Arg Cys Val Val His Gly Ala Glu Phe Trp Ser Gln
            175                 180                 185         190

TAC CGG ATT AAT GTG ACT GAG GTG AAC CCA CTG GGT GGT GCC AGC ACA  745
Tyr Arg Ile Asn Val Thr Glu Val Asn Pro Leu Gly Gly Ala Ser Thr
            195                 200                 205

CGC CTG CTG GAT GTG AGC TTG CAG AGC TTG ATC TTG CGC CCT GAC CCC  793
Arg Leu Leu Asp Val Ser Leu Gln Ser Leu Ile Leu Arg Pro Asp Pro
            210                 215                 220

CAG GGC CTG CGG GTA GAG TCA CCA GGT TAC CCC CGA GGC CTG CGA      841
Gln Gly Leu Arg Val Glu Ser Pro Gly Tyr Pro Arg Gly Leu Arg
            225                 230                 235
```

FIG. 8B

```
GCC AGC TGG ACA TAC CCT GCC TCC TGG CCG TGC CAG CCC CAC TTC CTG    889
Ala Ser Trp Thr Tyr Pro Ala Ser Trp Pro Cys Gln Pro His Phe Leu
240                 245                 250

CTC AAG TTC CGT TTG CAG TAC CGT CCG CAG CAT CCA GCC TGG TCC        937
Leu Lys Phe Arg Leu Gln Tyr Arg Pro Gln His Pro Ala Trp Ser
        255                 260                 265         270

ACG GTG GAG CCA GCT CTG GGA GAG GTG ATC ACA GAT GCT GTG GCT        985
Thr Val Glu Pro Ala Leu Gly Glu Val Ile Thr Asp Ala Val Ala
                275                 280                 285

GGG CTG CCC CAT GTA CGA GTC AGT GCC CGG GAC TTT CTA GAT GCT       1033
Gly Leu Pro His Val Arg Val Ser Ala Arg Asp Phe Leu Asp Ala
        290                 295                 300

GGC ACC TGG AGC ACC TGG AGC CCG GAG GCC TGG GGC ACT CCG AGC ACT   1081
Gly Thr Trp Ser Thr Trp Ser Pro Glu Ala Trp Gly Thr Pro Ser Thr
                305                 310                 315

GGG ACC ATA CCA AAG GAG ATA CCA GCA TGG GGC CAG CTA CAC ACG CAG   1129
Gly Thr Ile Pro Lys Glu Ile Pro Ala Trp Gly Gln Leu His Thr Gln
320                 325                 330

CCA GAG GTG GAG CCT GTG CAG GTG GAC AGC CCT GCT CCT CCA AGG CCC TCC 1177
Pro Glu Val Glu Pro Val Gln Val Asp Ser Pro Ala Pro Arg Pro Ser
        335                 340                 345         350

CTC CAA CCA CAC CCT CGG CTA CTT GAT CAC AGG GAC TCT GTG GAG CAG   1225
Leu Gln Pro His Pro Arg Leu Leu Asp His Arg Asp Ser Val Glu Gln
                355                 360                 365
```

FIG.8C

```
GTA GCT GTG CTG GCG TCT TTG GGA ATC CTT TCT TTC CTG GGA CTG GTG        1273
Val Ala Val Leu Ala Ser Leu Gly Ile Leu Ser Phe Leu Gly Leu Val
                370                             375                380

GCT GGG GCC CTG GCA CTG GGG CTC TGG CTG AGG CTG AGA CGG GGT GGG        1321
Ala Gly Ala Leu Ala Leu Gly Leu Trp Leu Arg Leu Arg Arg Gly Gly
        385                             390                 395

AAG GAT GGA TCC CCA AAG CCT GGG TTC TTG GCC TCA GTG ATT CCA GTG        1369
Lys Asp Gly Ser Pro Lys Pro Gly Phe Leu Ala Ser Val Ile Pro Val
    400                             405                 410

GAC AGG CGT CCA GGA GCT CCA AAC CTG TAGAGGACCC AGGAGGGCTT              1416
Asp Arg Arg Pro Gly Ala Pro Asn Leu
415                     420

CGGCAGATTC CACCTATAAT CCTGTCTTGC TGGTGTGGAT AGAAACCAGG CAGGACAGTA      1476

GATCCCTATG GTTGGATCTC AGCTGGAAGT TCTGTTTGGA GCCCATTTCT GTGAGACCCT      1536

GTATTTCAAA TTTGCAGCTG AAAGGTGCTT GTACCCTCGA TTTCACCCCA GAGTTGGAGT      1596

TCTGCTCAAG GAACGTGTGT AATGTGTACA TCTGTGTCCA TGTGTGACCA TGTGTCTGTG      1656

AAGCAGGGAA CATGTATTCT CTGCATGCAT GTATGTAGGT GCCTGGGGAG TGTGTGTGGG      1716

TCCTTGGCTC TTGCCTTTC CCCTTGCAGG GGTTGTGCAG GTGTGAATAA AGAGAATAAG      1776

GAAGTTCTTG GAGATTATAC TCAG                                              1800
```

FIG.8D

```
H1     MSSSCSGLSRVLVAVATALVSASSPCPQAWGPPGVQYGQP
M1     *******T***********S********************

H41    GRSVKLCCPGVTAGDPVSWFRDGEPKLLQGPDSGLGHELV
M41    **P*M****ST******DSR********R

H81    LAQADSTDEGTYICQTLDGALGGTVTLQLGYPPARPVVSC
M81    *VP***V**VSM*KF***E*

H121   QAADYENFSCTWSPSQISGLPTRYLTSYRKKTVLGADSQR
M121   V*********G*V**************LPE***

H161   RSPSTGPWPCPQDPLGAARCVVHGAEFWSQYRINVTEVNP
M161   E**************E*S*****************E**********

H201   LGGASTRLLDVSLQSILRPDPPQGLRVESVPGYPRRLRAS
M201   **#****C****R************************H**

H241   WTYPASWPCQPHFLLKFRLQYRPAQHPAWSTVEPAGLEEV
M240   *******RR***************************I*****

H281   ITDAVAGLPHAVRVSARDFLDAGTWSTWSPEAWGTPSTGT
M280   **************************A*************P

H321   IPKEIPAWGQLHTQP#E#VEPQVDSPAPPRPSLQPHPRLLD
M320   LQD***D*S*G*G*QL*A*VA*E***A**DP**

H360   HRDSVEQVAVLASLGILSFLGLVAGALALGLWLRLRRGGK
M361   *PL*********F*C*AV**********S

H400   DGSPKPGFLASVIPVDRRPGAPNL
M401   PQ*LPM*EKLI*QRTPENFS
```

FIG.9

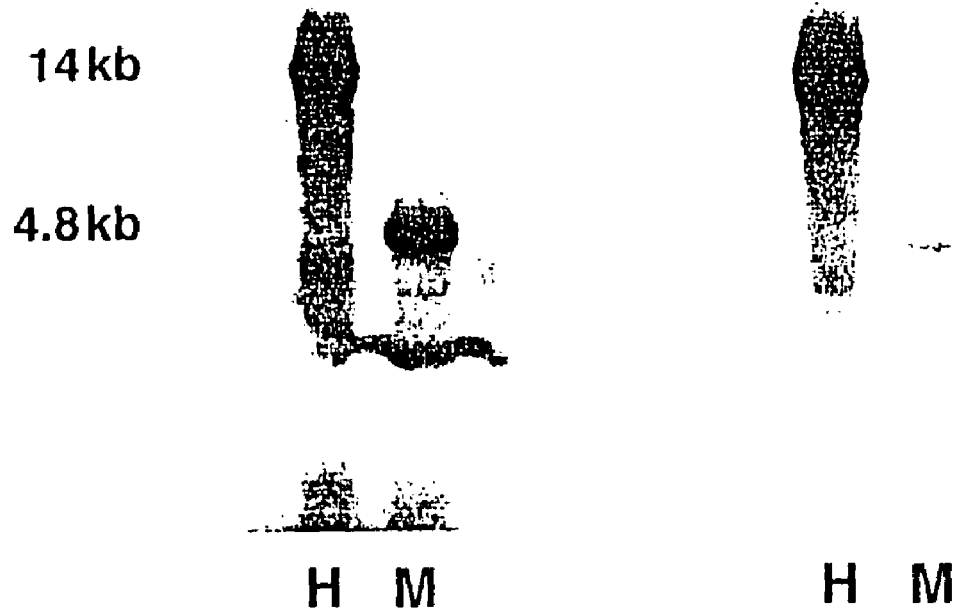

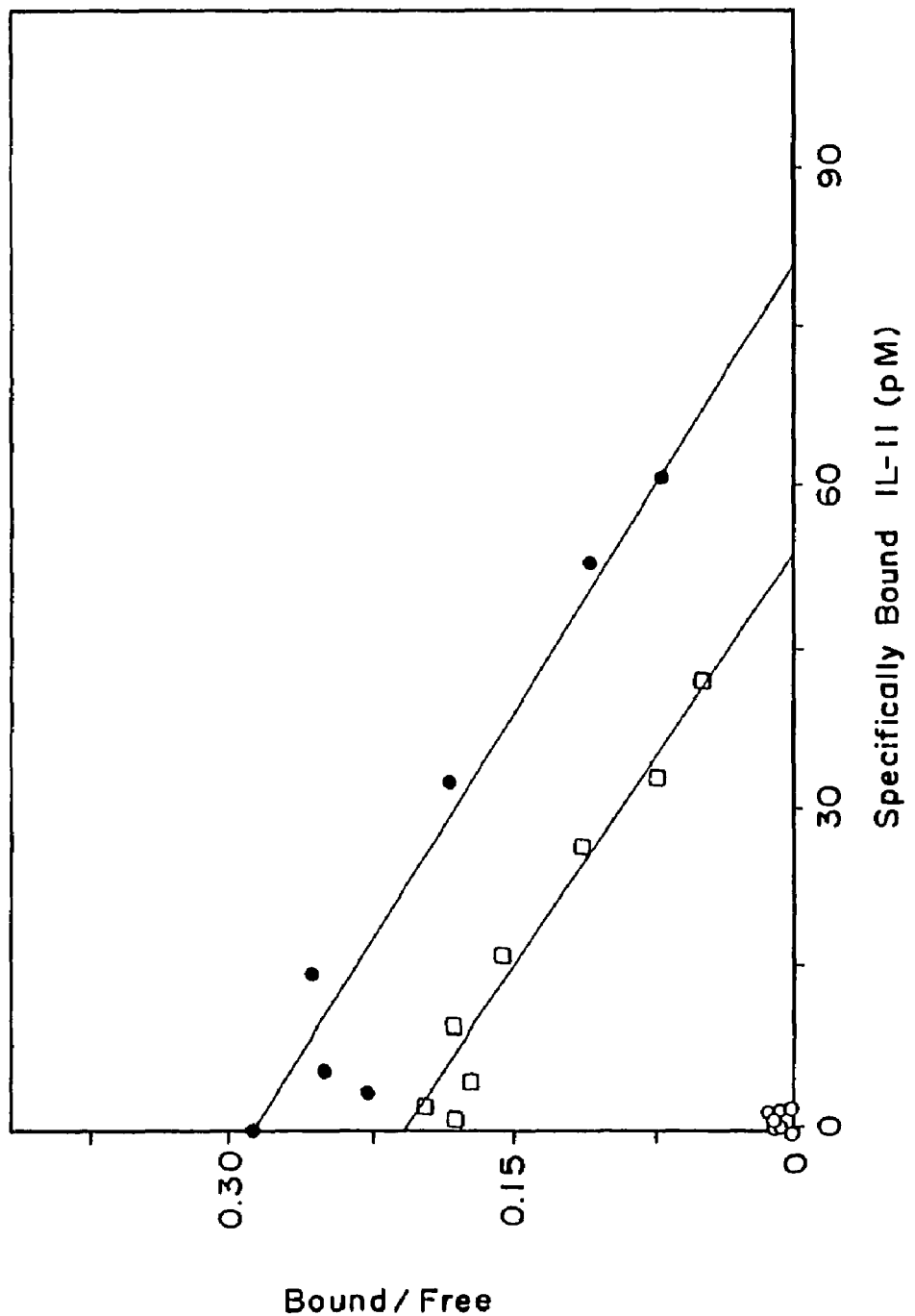

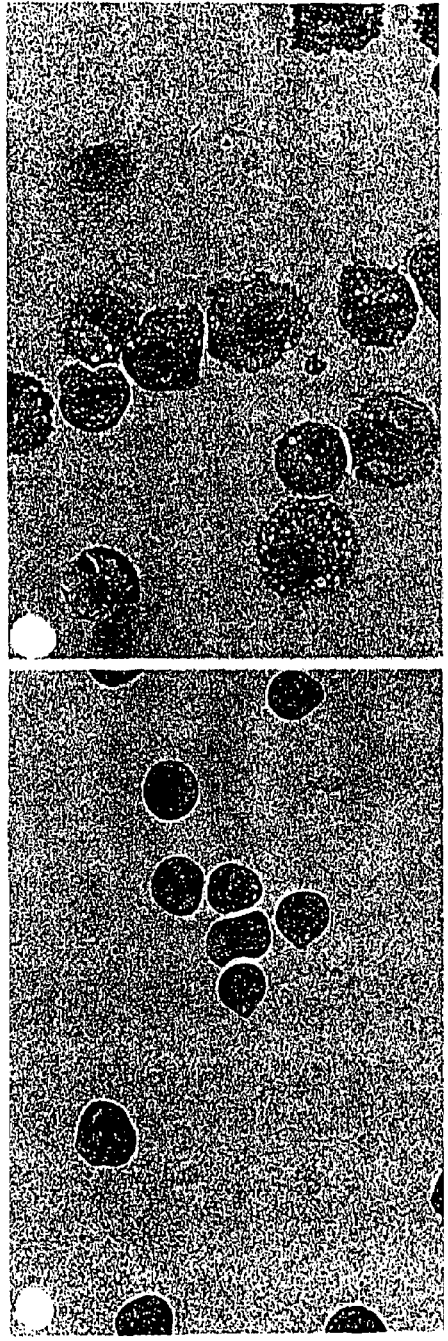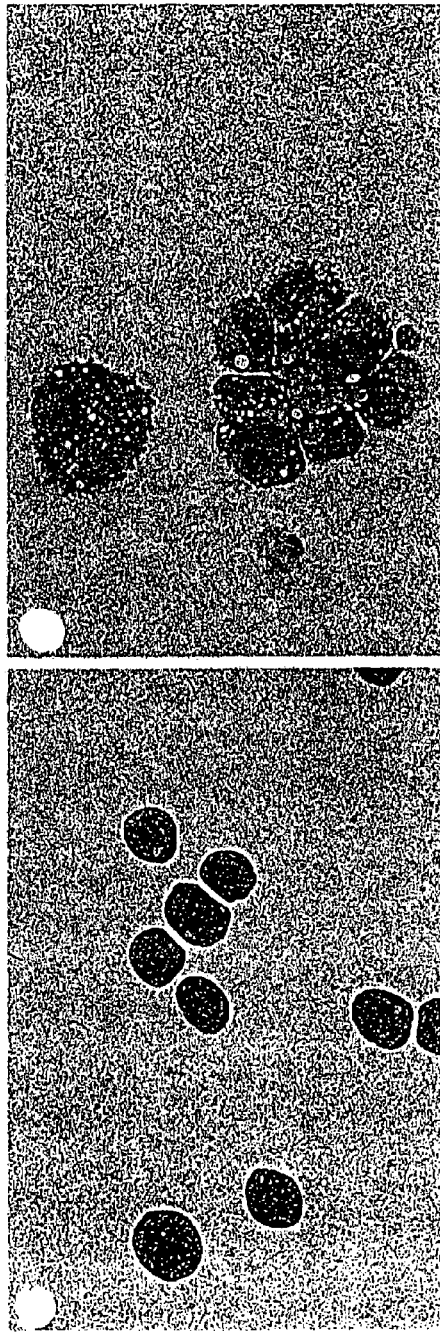

SEQUENCE LISTING (1) GENERAL INFORMATION:

(iii) NUMBER OF SEQUENCES: 25

(2) INFORMATION FOR SEQ ID NO: 1:

(i) SEQUENCE CHARACTERISTICS:
      (A) LENGTH: 5 amino acids
      (B) TYPE: amino acid
      (C) STRANDEDNESS: single
      (D) TOPOLOGY: linear (ii) MOLECULE TYPE: <Unknown>

(xi) SEQUENCE DESCRIPTION: SEQ ID NO: 1:

Trp Ser Xaa Trp Ser
1               5

(2) INFORMATION FOR SEQ ID NO: 2:

(i) SEQUENCE CHARACTERISTICS:
      (A) LENGTH: 1705 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 45..1340

(xi) SEQUENCE DESCRIPTION: SEQ ID NO: 2:

```
GAGAGGGTGA GGGCGGAGGC CGCTGGCGGC GGCTGCCGCA GAAG ATG AGC AGC AGC        56
                                                Met Ser Ser Ser
                                                 1

TGC TCA GGG CTG ACC AGG GTC CTG GTG GCC GTG GCT ACA GCC CTG GTG       104
Cys Ser Gly Leu Thr Arg Val Leu Val Ala Val Ala Thr Ala Leu Val
 5              10                  15                  20

TCT TCC TCC TCC CCC TGC CCC CAA GCT TGG GGT CCT CCA GGG GTC CAG       152
Ser Ser Ser Ser Pro Cys Pro Gln Ala Trp Gly Pro Pro Gly Val Gln
             25                  30                  35

TAT GGA CAA CCT GGC AGG CCC GTG ATG CTG TGC TGC CCC GGA GTG AGT       200
Tyr Gly Gln Pro Gly Arg Pro Val Met Leu Cys Cys Pro Gly Val Ser
         40                  45                  50

GCT GGG ACT CCA GTG TCC TGG TTT CGG GAT GGA GAT TCA AGG CTG CTC       248
Ala Gly Thr Pro Val Ser Trp Phe Arg Asp Gly Asp Ser Arg Leu Leu
     55                  60                  65

CAG GGA CCT GAC TCT GGG TTA GGA CAC AGA CTG GTC TTG GCC CAG GTG       296
Gln Gly Pro Asp Ser Gly Leu Gly His Arg Leu Val Leu Ala Gln Val
 70                  75                  80

GAC AGC CCT GAT GAA GGC ACT TAT GTC TGC CAG ACC CTG GAT GGT GTA       344
Asp Ser Pro Asp Glu Gly Thr Tyr Val Cys Gln Thr Leu Asp Gly Val
 85                  90                  95                 100

TCA GGG GGC ATG GTG ACC CTG AAG CTG GGC TTT CCC CCA GCA CGT CCT       392
Ser Gly Gly Met Val Thr Leu Lys Leu Gly Phe Pro Pro Ala Arg Pro
                105                 110                 115

GAA GTC TCC TGC CAA GCG GTA GAC TAT GAA AAC TTC TCC TGT ACT TGG       440
Glu Val Ser Cys Gln Ala Val Asp Tyr Glu Asn Phe Ser Cys Thr Trp
            120                 125                 130

AGT CCA GGC CAG GTC AGC GGT TTG CCC ACC CGC TAC CTT ACT TCC TAC       488
Ser Pro Gly Gln Val Ser Gly Leu Pro Thr Arg Tyr Leu Thr Ser Tyr
        135                 140                 145
```

```
AGG AAG AAG ACG CTG CCA GGA GCT GAG AGT CAG AGG GAA AGT CCA TCC      536
Arg Lys Lys Thr Leu Pro Gly Ala Glu Ser Gln Arg Glu Ser Pro Ser
    150                 155                 160

ACC GGG CCT TGG CCG TGT CCA CAG GAC CCT CTG GAG GCC TCC CGA TGT      584
Thr Gly Pro Trp Pro Cys Pro Gln Asp Pro Leu Glu Ala Ser Arg Cys
165                 170                 175                 180

GTG GTC CAT GGG GCA GAG TTC TGG AGT GAG TAC CGG ATC AAT GTG ACC      632
Val Val His Gly Ala Glu Phe Trp Ser Glu Tyr Arg Ile Asn Val Thr
                185                 190                 195

GAG GTG AAC CCA CTG GGT GCC AGC ACG TGC CTA CTG GAT GTG AGA TTA      680
Glu Val Asn Pro Leu Gly Ala Ser Thr Cys Leu Leu Asp Val Arg Leu
            200                 205                 210

CAG AGC ATC TTG CGT CCT GAT CCA CCC CAA GGA CTG CGG GTG GAA TCC      728
Gln Ser Ile Leu Arg Pro Asp Pro Pro Gln Gly Leu Arg Val Glu Ser
        215                 220                 225

GTA CCT GGT TAC CCG AGA CGC CTG CAT GCC AGC TGG ACA TAC CCT GCC      776
Val Pro Gly Tyr Pro Arg Arg Leu His Ala Ser Trp Thr Tyr Pro Ala
    230                 235                 240

TCC TGG CGT CGC CAA CCC CAC TTT CTG CTC AAG TTC CGG TTG CAA TAC      824
Ser Trp Arg Arg Gln Pro His Phe Leu Leu Lys Phe Arg Leu Gln Tyr
245                 250                 255                 260

CGA CCA GCA CAG CAT CCA GCC TGG TCC ACG GTG GAG CCC ATT GGC TTG      872
Arg Pro Ala Gln His Pro Ala Trp Ser Thr Val Glu Pro Ile Gly Leu
                265                 270                 275

GAG GAA GTG ATA ACA GAT GCT GTG GCT GGG CTG CCA CAC GCG GTA CGA      920
Glu Glu Val Ile Thr Asp Ala Val Ala Gly Leu Pro His Ala Val Arg
            280                 285                 290

GTC AGT GCC AGG GAC TTT CTG GAT GCT GGC ACC TGG AGC GCC TGG AGC      968
Val Ser Ala Arg Asp Phe Leu Asp Ala Gly Thr Trp Ser Ala Trp Ser
        295                 300                 305

CCA GAG GCC TGG GGT ACT CCT AGC ACT GGT CCC CTG CAG GAT GAG ATA     1016
Pro Glu Ala Trp Gly Thr Pro Ser Thr Gly Pro Leu Gln Asp Glu Ile
    310                 315                 320

CCT GAT TGG AGC CAG GGA CAT GGA CAG CAG CTA GAG GCA GTA GTA GCT     1064
Pro Asp Trp Ser Gln Gly His Gly Gln Gln Leu Glu Ala Val Val Ala
325                 330                 335                 340

CAG GAG GAC AGC CCG GCT CCT GCA AGG CCT TCC TTG CAG CCG GAC CCA     1112
Gln Glu Asp Ser Pro Ala Pro Ala Arg Pro Ser Leu Gln Pro Asp Pro
                345                 350                 355

AGG CCA CTT GAT CAC AGG GAC CCC TTG GAG CAA GTA GCT GTG TTA GCG     1160
Arg Pro Leu Asp His Arg Asp Pro Leu Glu Gln Val Ala Val Leu Ala
            360                 365                 370

TCT CTG GGA ATC TTC TCT TGC CTT GGC CTG GCT GTT GGA GCT CTG GCA     1208
Ser Leu Gly Ile Phe Ser Cys Leu Gly Leu Ala Val Gly Ala Leu Ala
        375                 380                 385

CTG GGG CTC TGG CTG AGG CTG AGA CGG AGT GGG AAG GAT GGA CCG CAA     1256
Leu Gly Leu Trp Leu Arg Leu Arg Arg Ser Gly Lys Asp Gly Pro Gln
    390                 395                 400

AAA CCT GGG CTC TTG GCA CCC ATG ATC CCG GTG GAA AAG CTT CCA GGA     1304
Lys Pro Gly Leu Leu Ala Pro Met Ile Pro Val Glu Lys Leu Pro Gly
405                 410                 415                 420

ATT CCA AAC CTG CAG AGG ACC CCA GAG AAC TTC AGC TGATTTCATC          1350
Ile Pro Asn Leu Gln Arg Thr Pro Glu Asn Phe Ser
                425                 430

TGTAACCCGG TCAGACTGGG GGCAGAAAGA GGCGGGGCAG TGGATCCCTG TGGATGGAGG   1410

TCTCAGCTGA AAGTCTGAGC TCTTTTCTTT GACACCTATA CTCCAAACTT GCTGCCGGCT   1470

GAAGGCTGTC TGGACTTCCG ATGTCCTGAG GTGGAAGTCC ACCTGAGGAA TGTGTACAGA   1530

AGTCTGTGTT CCTGTGATCG TGTGTGTATG TGAGACAGGG AGCAAAAGTT CTCTGCATGT   1590
```

```
GTGTACAGAT GATTGGAGAG TGTGTGCGGT CTTGGGCTTG GCCCTTCTGG GAAGTGTGAA      1650

GAGTTGAAAT AAAAGAGACG GAAGTTTTTG GAAAAAAAAA AAAAAAAAAA AAAAA           1705
```

(2) INFORMATION FOR SEQ ID NO: 3:

(i) SEQUENCE CHARACTERISTICS:
        (A) LENGTH: 432 amino acids
        (B) TYPE: amino acid
        (D) TOPOLOGY: linear (ii) MOLECULE TYPE: protein (xi) SEQUENCE DESCRIPTION: SEQ ID NO: 3:

```
Met Ser Ser Ser Cys Ser Gly Leu Thr Arg Val Leu Val Ala Val Ala
  1               5                  10                  15

Thr Ala Leu Val Ser Ser Ser Pro Cys Pro Gln Ala Trp Gly Pro
             20                  25                  30

Pro Gly Val Gln Tyr Gly Gln Pro Gly Arg Pro Val Met Leu Cys Cys
             35                  40                  45

Pro Gly Val Ser Ala Gly Thr Pro Val Ser Trp Phe Arg Asp Gly Asp
 50                  55                  60

Ser Arg Leu Leu Gln Gly Pro Asp Ser Gly Leu Gly His Arg Leu Val
 65                  70                  75                  80

Leu Ala Gln Val Asp Ser Pro Asp Glu Gly Thr Tyr Val Cys Gln Thr
                 85                  90                  95

Leu Asp Gly Val Ser Gly Gly Met Val Thr Leu Lys Leu Gly Phe Pro
                100                 105                 110

Pro Ala Arg Pro Glu Val Ser Cys Gln Ala Val Asp Tyr Glu Asn Phe
             115                 120                 125

Ser Cys Thr Trp Ser Pro Gly Gln Val Ser Gly Leu Pro Thr Arg Tyr
130                 135                 140

Leu Thr Ser Tyr Arg Lys Lys Thr Leu Pro Gly Ala Glu Ser Gln Arg
145                 150                 155                 160

Glu Ser Pro Ser Thr Gly Pro Trp Pro Cys Pro Gln Asp Pro Leu Glu
                165                 170                 175

Ala Ser Arg Cys Val Val His Gly Ala Glu Phe Trp Ser Glu Tyr Arg
                180                 185                 190

Ile Asn Val Thr Glu Val Asn Pro Leu Gly Ala Ser Thr Cys Leu Leu
            195                 200                 205

Asp Val Arg Leu Gln Ser Ile Leu Arg Pro Asp Pro Pro Gln Gly Leu
210                 215                 220

Arg Val Glu Ser Val Pro Gly Tyr Pro Arg Arg Leu His Ala Ser Trp
225                 230                 235                 240

Thr Tyr Pro Ala Ser Trp Arg Arg Gln Pro His Phe Leu Leu Lys Phe
                245                 250                 255

Arg Leu Gln Tyr Arg Pro Ala Gln His Pro Ala Trp Ser Thr Val Glu
                260                 265                 270

Pro Ile Gly Leu Glu Glu Val Ile Thr Asp Ala Val Ala Gly Leu Pro
            275                 280                 285

His Ala Val Arg Val Ser Ala Arg Asp Phe Leu Asp Ala Gly Thr Trp
290                 295                 300

Ser Ala Trp Ser Pro Glu Ala Trp Gly Thr Pro Ser Thr Gly Pro Leu
305                 310                 315                 320

Gln Asp Glu Ile Pro Asp Trp Ser Gln Gly His Gly Gln Gln Leu Glu
                325                 330                 335
```

```
Ala Val Val Ala Gln Glu Asp Ser Pro Ala Pro Ala Arg Pro Ser Leu
            340                 345                 350

Gln Pro Asp Pro Arg Pro Leu Asp His Arg Asp Pro Leu Glu Gln Val
        355                 360                 365

Ala Val Leu Ala Ser Leu Gly Ile Phe Ser Cys Leu Gly Leu Ala Val
    370                 375                 380

Gly Ala Leu Ala Leu Gly Leu Trp Leu Arg Leu Arg Arg Ser Gly Lys
385                 390                 395                 400

Asp Gly Pro Gln Lys Pro Gly Leu Leu Ala Pro Met Ile Pro Val Glu
                405                 410                 415

Lys Leu Pro Gly Ile Pro Asn Leu Gln Arg Thr Pro Glu Asn Phe Ser
            420                 425                 430
```

(2) INFORMATION FOR SEQ ID NO: 4:

(i) SEQUENCE CHARACTERISTICS:
        (A) LENGTH: 1800 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 128..1396

(xi) SEQUENCE DESCRIPTION: SEQ ID NO: 4:

```
TCTAACAGCC TTACCCCACT TGGTGCATCA ATTTTTCTCC TAGGAAGCCT CAGTTTTGGA      60

GAGGAAGAGC CAGGCTTTAG CTCCCATCTC AGGGGTCGGG GATTTTTGAC TCTACCTCTC     120

CCCACAG ATG AGC AGC AGC TGC TCA GGG CTG AGC AGG GTC CTG GTG GCC       169
        Met Ser Ser Ser Cys Ser Gly Leu Ser Arg Val Leu Val Ala
            435                 440                 445

GTG GCT ACA GCC CTG GTG TCT GCC TCC TCC CCC TGC CCC CAG GCC TGG       217
Val Ala Thr Ala Leu Val Ser Ala Ser Ser Pro Cys Pro Gln Ala Trp
        450                 455                 460

GGC CCC CCA GGG GTC CAG TAT GGG CAG CCA GGC AGG TCC GTG AAG CTG       265
Gly Pro Pro Gly Val Gln Tyr Gly Gln Pro Gly Arg Ser Val Lys Leu
    465                 470                 475

TGT TGT CCT GGA GTG ACT GCC GGG GAC CCA GTG TCC TGG TTT CGG GAT       313
Cys Cys Pro Gly Val Thr Ala Gly Asp Pro Val Ser Trp Phe Arg Asp
    480                 485                 490

GGG GAG CCA AAG CTG CTC CAG GGA CCT GAC TCT GGG CTA GGG CAT GAA       361
Gly Glu Pro Lys Leu Leu Gln Gly Pro Asp Ser Gly Leu Gly His Glu
495                 500                 505                 510

CTG GTC CTG GCC CAG GCA GAC AGC ACT GAT GAG GGC ACC TAC ATC TGC       409
Leu Val Leu Ala Gln Ala Asp Ser Thr Asp Glu Gly Thr Tyr Ile Cys
            515                 520                 525

CAG ACC CTG GAT GGT GCA CTT GGG GGC ACA GTG ACC CTG CAG CTG GGC       457
Gln Thr Leu Asp Gly Ala Leu Gly Gly Thr Val Thr Leu Gln Leu Gly
        530                 535                 540

TAC CCT CCA GCC CGC CCT GTT GTC TCC TGC CAA GCA GCC GAC TAT GAG       505
Tyr Pro Pro Ala Arg Pro Val Val Ser Cys Gln Ala Ala Asp Tyr Glu
    545                 550                 555

AAC TTC TCT TGC ACT TGG AGT CCC AGC CAG ATC AGC GGT TTA CCC ACC       553
Asn Phe Ser Cys Thr Trp Ser Pro Ser Gln Ile Ser Gly Leu Pro Thr
    560                 565                 570

CGC TAC CTC ACC TCC TAC AGG AAG AAG ACA GTC CTA GGA GCT GAT AGC       601
Arg Tyr Leu Thr Ser Tyr Arg Lys Lys Thr Val Leu Gly Ala Asp Ser
575                 580                 585                 590
```

```
CAG AGG AGG AGT CCA TCC ACA GGG CCC TGG CCA TGC CCA CAG GAT CCC        649
Gln Arg Arg Ser Pro Ser Thr Gly Pro Trp Pro Cys Pro Gln Asp Pro
            595                 600                 605

CTA GGG GCT GCC CGC TGT GTT GTC CAC GGG GCT GAG TTC TGG AGC CAG        697
Leu Gly Ala Ala Arg Cys Val Val His Gly Ala Glu Phe Trp Ser Gln
        610                 615                 620

TAC CGG ATT AAT GTG ACT GAG GTG AAC CCA CTG GGT GGT GCC AGC ACA        745
Tyr Arg Ile Asn Val Thr Glu Val Asn Pro Leu Gly Gly Ala Ser Thr
                625                 630                 635

CGC CTG CTG GAT GTG AGC TTG CAG AGC ATC TTG CGC CCT GAC CCA CCC        793
Arg Leu Leu Asp Val Ser Leu Gln Ser Ile Leu Arg Pro Asp Pro Pro
        640                 645                 650

CAG GGC CTG CGG GTA GAG TCA GTA CCA GGT TAC CCC CGA GGC CTG CGA        841
Gln Gly Leu Arg Val Glu Ser Val Pro Gly Tyr Pro Arg Gly Leu Arg
655                 660                 665                 670

GCC AGC TGG ACA TAC CCT GCC TCC TGG CCG TGC AGC CCC CAC TTC CTG        889
Ala Ser Trp Thr Tyr Pro Ala Ser Trp Pro Cys Ser Pro His Phe Leu
                675                 680                 685

CTC AAG TTC CGT TTG CAG TAC CGT CCG GCG CAG CAT CCA GCC TGG TCC        937
Leu Lys Phe Arg Leu Gln Tyr Arg Pro Ala Gln His Pro Ala Trp Ser
        690                 695                 700

ACG GTG GAG CCA GCT GGA CTG GAG GAG GTG ATC ACA GAT GCT GTG GCT        985
Thr Val Glu Pro Ala Gly Leu Glu Glu Val Ile Thr Asp Ala Val Ala
            705                 710                 715

GGG CTG CCC CAT GCT GTA CGA GTC AGT GCC CGG GAC TTT CTA GAT GCT       1033
Gly Leu Pro His Ala Val Arg Val Ser Ala Arg Asp Phe Leu Asp Ala
        720                 725                 730

GGC ACC TGG AGC ACC TGG AGC CCG GAG GCC TGG GGA ACT CCG AGC ACT       1081
Gly Thr Trp Ser Thr Trp Ser Pro Glu Ala Trp Gly Thr Pro Ser Thr
735                 740                 745                 750

GGG ACC ATA CCA AAG GAG ATA CCA GCA TGG GGC CAG CTA CAC ACG CAG       1129
Gly Thr Ile Pro Lys Glu Ile Pro Ala Trp Gly Gln Leu His Thr Gln
                755                 760                 765

CCA GAG GTG GAG CCT CAG GTG GAC AGC CCT GCT CCT CCA AGG CCC TCC       1177
Pro Glu Val Glu Pro Gln Val Asp Ser Pro Ala Pro Pro Arg Pro Ser
        770                 775                 780

CTC CAA CCA CAC CCT CGG CTA CTT GAT CAC AGG GAC TCT GTG GAG CAG       1225
Leu Gln Pro His Pro Arg Leu Leu Asp His Arg Asp Ser Val Glu Gln
            785                 790                 795

GTA GCT GTG CTG GCG TCT TTG GGA ATC CTT TCT TTC CTG GGA CTG GTG       1273
Val Ala Val Leu Ala Ser Leu Gly Ile Leu Ser Phe Leu Gly Leu Val
        800                 805                 810

GCT GGG GCC CTG GCA CTG GGG CTC TGG CTG AGG CTG AGA CGG GGT GGG       1321
Ala Gly Ala Leu Ala Leu Gly Leu Trp Leu Arg Leu Arg Arg Gly Gly
815                 820                 825                 830

AAG GAT GGA TCC CCA AAG CCT GGG TTC TTG GCC TCA GTG ATT CCA GTG       1369
Lys Asp Gly Ser Pro Lys Pro Gly Phe Leu Ala Ser Val Ile Pro Val
                835                 840                 845

GAC AGG CGT CCA GGA GCT CCA AAC CTG TAGAGGACCC AGGAGGGCTT             1416
Asp Arg Arg Pro Gly Ala Pro Asn Leu
        850                 855

CGGCAGATTC CACCTATAAT CCTGTCTTGC TGGTGTGGAT AGAAACCAGG CAGGACAGTA     1476

GATCCCTATG GTTGGATCTC AGCTGGAAGT TCTGTTTGGA GCCCATTTCT GTGAGACCCT     1536

GTATTTCAAA TTTGCAGCTG AAAGGTGCTT GTACCTCTGA TTTCACCCCA GAGTTGGAGT     1596

TCTGCTCAAG GAACGTGTGT AATGTGTACA TCTGTGTCCA TGTGTGACCA TGTGTCTGTG     1656

AAGCAGGGAA CATGTATTCT CTGCATGCAT GTATGTAGGT GCCTGGGGAG TGTGTGTGGG     1716
```

-continued

```
TCCTTGGCTC TTGGCCTTTC CCCTTGCAGG GGTTGTGCAG GTGTGAATAA AGAGAATAAG    1776

GAAGTTCTTG GAGATTATAC TCAG                                           1800

(2) INFORMATION FOR SEQ ID NO: 5:

(i) SEQUENCE CHARACTERISTICS:
        (A) LENGTH: 423 amino acids
        (B) TYPE: amino acid
        (D) TOPOLOGY: linear (ii) MOLECULE TYPE: protein (xi) SEQUENCE DESCRIPTION: SEQ ID NO: 5:

Met Ser Ser Ser Cys Ser Gly Leu Ser Arg Val Leu Val Ala Val Ala
 1               5                  10                  15

Thr Ala Leu Val Ser Ala Ser Pro Cys Pro Gln Ala Trp Gly Pro
             20                  25                  30

Pro Gly Val Gln Tyr Gly Gln Pro Gly Arg Ser Val Lys Leu Cys Cys
             35                  40                  45

Pro Gly Val Thr Ala Gly Asp Pro Val Ser Trp Phe Arg Asp Gly Glu
 50                  55                  60

Pro Lys Leu Leu Gln Gly Pro Asp Ser Gly Leu Gly His Glu Leu Val
 65                  70                  75                  80

Leu Ala Gln Ala Asp Ser Thr Asp Glu Gly Thr Tyr Ile Cys Gln Thr
                 85                  90                  95

Leu Asp Gly Ala Leu Gly Gly Thr Val Thr Leu Gln Leu Gly Tyr Pro
             100                 105                 110

Pro Ala Arg Pro Val Val Ser Cys Gln Ala Ala Asp Tyr Glu Asn Phe
             115                 120                 125

Ser Cys Thr Trp Ser Pro Ser Gln Ile Ser Gly Leu Pro Thr Arg Tyr
 130                 135                 140

Leu Thr Ser Tyr Arg Lys Lys Thr Val Leu Gly Ala Asp Ser Gln Arg
145                 150                 155                 160

Arg Ser Pro Ser Thr Gly Pro Trp Pro Cys Pro Gln Asp Pro Leu Gly
                 165                 170                 175

Ala Ala Arg Cys Val Val His Gly Ala Glu Phe Trp Ser Gln Tyr Arg
             180                 185                 190

Ile Asn Val Thr Glu Val Asn Pro Leu Gly Gly Ala Ser Thr Arg Leu
             195                 200                 205

Leu Asp Val Ser Leu Gln Ser Ile Leu Arg Pro Asp Pro Pro Gln Gly
 210                 215                 220

Leu Arg Val Glu Ser Val Pro Gly Tyr Pro Arg Gly Leu Arg Ala Ser
225                 230                 235                 240

Trp Thr Tyr Pro Ala Ser Trp Pro Cys Gln Pro His Phe Leu Leu Lys
                 245                 250                 255

Phe Arg Leu Gln Tyr Arg Pro Ala Gln His Pro Ala Trp Ser Thr Val
             260                 265                 270

Glu Pro Ala Gly Leu Glu Glu Val Ile Thr Asp Ala Val Ala Gly Leu
             275                 280                 285

Pro His Ala Val Arg Val Ser Ala Arg Asp Phe Leu Asp Ala Gly Thr
             290                 295                 300

Trp Ser Thr Trp Ser Pro Glu Ala Trp Gly Thr Pro Ser Thr Gly Thr
305                 310                 315                 320

Ile Pro Lys Glu Ile Pro Ala Trp Gly Gln Leu His Thr Gln Pro Glu
                 325                 330                 335
```

```
Val Glu Pro Gln Val Asp Ser Pro Ala Pro Pro Arg Pro Ser Leu Gln
            340                 345                 350

Pro His Pro Arg Leu Leu Asp His Arg Asp Ser Val Glu Gln Val Ala
            355                 360                 365

Val Leu Ala Ser Leu Gly Ile Leu Ser Phe Leu Gly Leu Val Ala Gly
    370                 375                 380

Ala Leu Ala Leu Gly Leu Trp Leu Arg Leu Arg Arg Gly Gly Lys Asp
385                 390                 395                 400

Gly Ser Pro Lys Pro Gly Phe Leu Ala Ser Val Ile Pro Val Asp Arg
                405                 410                 415

Arg Pro Gly Ala Pro Asn Leu
            420

(2) INFORMATION FOR SEQ ID NO: 6:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..2
        (D) OTHER INFORMATION: /note= "R at Position 1 is A or G"

(ix) FEATURE:
        (A) NAME/KEY: misc_feature
        (B) LOCATION: 7..8
        (D) OTHER INFORMATION: /note= "Y at Position 7 is C or T"

(ix) FEATURE:
        (A) NAME/KEY: misc_feature
        (B) LOCATION: 10..11
        (D) OTHER INFORMATION: /note= "R at Position 10 is A or G"

(xi) SEQUENCE DESCRIPTION: SEQ ID NO: 6:

RCTCCAYTCR CTCCA                                              15

(2) INFORMATION FOR SEQ ID NO: 7:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..2
        (D) OTHER INFORMATION: /note= "R at Position 1 is A or G"

(ix) FEATURE:
        (A) NAME/KEY: misc_feature
        (B) LOCATION: 7..8
        (D) OTHER INFORMATION: /note= "R at Position 7 is A or G"

(ix) FEATURE:
        (A) NAME/KEY: misc_feature
        (B) LOCATION: 10..11
        (D) OTHER INFORMATION: /note= "R at Position 10 is A or G"

(xi) SEQUENCE DESCRIPTION: SEQ ID NO: 7:

RCTCCARTCR CTCCA                                              15
```

(2) INFORMATION FOR SEQ ID NO: 8:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..2
        (D) OTHER INFORMATION: /note= "R at Position 1 is A or G"

(ix) FEATURE:
        (A) NAME/KEY: misc_feature
        (B) LOCATION: 7..8
        (D) OTHER INFORMATION: /note= "N at Position 7 is N"

(ix) FEATURE:
        (A) NAME/KEY: misc_feature
        (B) LOCATION: 10..11
        (D) OTHER INFORMATION: /note= "R at Position 10 is A or G"

(xi) SEQUENCE DESCRIPTION: SEQ ID NO: 8:

RCTCCANGCR CTCCA                                        15

(2) INFORMATION FOR SEQ ID NO: 9:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..2
        (D) OTHER INFORMATION: /note= "R at Position 1 is A or G"

(ix) FEATURE:
        (A) NAME/KEY: misc_feature
        (B) LOCATION: 7..8
        (D) OTHER INFORMATION: /note= "N at Position 7 is N"

(ix) FEATURE:
        (A) NAME/KEY: misc_feature
        (B) LOCATION: 10..11
        (D) OTHER INFORMATION: /note= "R at Position 10 is A or G"

(xi) SEQUENCE DESCRIPTION: SEQ ID NO: 9:

RCTCCANGGR CTCCA                                        15

(2) INFORMATION FOR SEQ ID NO: 10:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: misc_feature
        (B) LOCATION: 1..2
        (D) OTHER INFORMATION: /note= "R at Position 1 is A or G"

(ix) FEATURE:
        (A) NAME/KEY: misc_feature
        (B) LOCATION: 7..8
        (D) OTHER INFORMATION: /note= "Y at Position 7 is C or T"

(ix) FEATURE:
            (A) NAME/KEY: misc_feature
            (B) LOCATION: 10..11
            (D) OTHER INFORMATION: /note= "R at Position 10 is A or G"

(xi) SEQUENCE DESCRIPTION: SEQ ID NO: 10:

RCTCCAYTTR CTCCA                                                              15

(2) INFORMATION FOR SEQ ID NO: 11:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 11:

TGGTCCACGG TGGAGCCCAT TGGCT                                                   25

(2) INFORMATION FOR SEQ ID NO: 12:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO: 12:

CCACACGCGG TACGAGTCAG TGCCAGGGAC                                              30

(2) INFORMATION FOR SEQ ID NO: 13:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO: 13:

AGCAAGTTCA GCCTGGTTAA G                                                       21

(2) INFORMATION FOR SEQ ID NO: 14:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO: 14:

CTTATGAGTA TTTCTTCCAG GGTA                                                    24

(2) INFORMATION FOR SEQ ID NO: 15:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 15:

CCCTTCATTG ACCTCAACTA CATG                                            24

(2) INFORMATION FOR SEQ ID NO: 16:

(i) SEQUENCE CHARACTERISTICS:
           (A) LENGTH: 24 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO: 16:

CATGCCAGTG AGCTTCCCGT TCAG                                            24

(2) INFORMATION FOR SEQ ID NO: 17:

(i) SEQUENCE CHARACTERISTICS:
           (A) LENGTH: 24 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO: 17:

GGGTCCTCCA GGGGTCCAGT ATGG                                            24

(2) INFORMATION FOR SEQ ID NO: 18:

(i) SEQUENCE CHARACTERISTICS:
           (A) LENGTH: 17 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO: 18:

GGAGGCCTCC AGAGGGT                                                    17

(2) INFORMATION FOR SEQ ID NO: 19:

(i) SEQUENCE CHARACTERISTICS:
           (A) LENGTH: 21 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO: 19:

CTCCTGTACT TGGAGTCCAG G                                               21

(2) INFORMATION FOR SEQ ID NO: 20:

(i) SEQUENCE CHARACTERISTICS:
           (A) LENGTH: 30 base pairs
           (B) TYPE: nucleic acid
           (C) STRANDEDNESS: single
           (D) TOPOLOGY: linear (ii) MOLECULE TYPE: DNA (genomic)

```
        (xi) SEQUENCE DESCRIPTION: SEQ ID NO: 20:

GGAAAGCTGT GGCGTGATGG CCGTGGGGCA                                    30

(2) INFORMATION FOR SEQ ID NO: 21:

(i) SEQUENCE CHARACTERISTICS:
             (A) LENGTH: 22 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO: 21:

GGGCGGAGGC CGCTGGCGGG CG                                            22

(2) INFORMATION FOR SEQ ID NO: 22:

(i) SEQUENCE CHARACTERISTICS:
             (A) LENGTH: 23 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO: 22:

TTATCAGCTG AAGTTCTCTG GGG                                           23

(2) INFORMATION FOR SEQ ID NO: 23:

(i) SEQUENCE CHARACTERISTICS:
             (A) LENGTH: 15 base pairs
             (B) TYPE: nucleic acid
             (C) STRANDEDNESS: single
             (D) TOPOLOGY: linear (ii) MOLECULE TYPE: DNA (genomic)

(ix) FEATURE:
             (A) NAME/KEY: misc_feature
             (B) LOCATION: 1..2
             (D) OTHER INFORMATION: /note= "R at Position 1 is G or A"

(ix) FEATURE:
             (A) NAME/KEY: misc_feature
             (B) LOCATION: 7..8
             (D) OTHER INFORMATION: /note= "N at Position 7 is N"

(ix) FEATURE:
             (A) NAME/KEY: misc_feature
             (B) LOCATION: 10..11
             (D) OTHER INFORMATION: /note= "R at Position 10 is G or A"

(xi) SEQUENCE DESCRIPTION: SEQ ID NO: 23:

RCTCCANGCR CTCAA                                                    15

(2) INFORMATION FOR SEQ ID NO: 24:

(i) SEQUENCE CHARACTERISTICS:
             (A) LENGTH: 28 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO: 24:

ATCTTCTAGA TCCCCCTGCC CCCAAGCT                                      28
```

-continued

```
(2) INFORMATION FOR SEQ ID NO: 25:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 25:

ACTTTCTAGA TTATTGCTCC AAGGGGTCCC TGTG                                34
```

NUCLEIC ACID ENCODING α CHAIN OF HUMAN IL-11 RECEPTOR

CROSS REFERENCE TO RELATED APPLICATIONS

The present application is a continuation of application Ser. No. 09/532,263, filed Mar. 22, 2000, now U.S. Pat. No. 7,002,000, which is a divisional of application Ser. No. 08/702,665, filed Dec. 20, 1996, now U.S. Pat. No. 6,274,708.

The present invention relates generally to novel haemopoietin receptors, or components or parts thereof and to a method for cloning genetic sequences encoding same. More particularly, the subject invention is directed to recombinant or synthetic haemopoietin receptors or components or parts thereof. The receptor molecules or components or parts thereof and their genetic sequences of the present invention are useful in the development of a wide range of agonists, antagonists and therapeutics and diagnostic reagents based on ligand interaction with its receptor.

Bibliographic details of the publications numerically referred to in this specification are collected at the end of the description. Sequence Identity Numbers (SEQ ID NOs.) for the nucleotide and amino acid sequences referred to in the specification are defined following the bibliography.

Throughout this specification and the claims which follow, unless the context requires otherwise, the word "comprise", or variations such as "comprises" or "comprising", will be understood to imply the inclusion of a stated integer or group of integers but not the exclusion of any other integer or group of integers.

The proliferation, differentiation and function of a wide variety of cells are controlled by secreted regulators, known as cytokines. One such cytokine is interleukin (IL)-11 which is a functionally pleiotropic molecule (1,2), initially characterized by its ability to stimulate proliferation of the IL-6-dependent plasmacytoma cell line, T11 65 (3). Other biological actions of IL-11 include induction of multipotential haemopoietin progenitor cell proliferation (4,5,6), enhancement of megakaryocyte and platelet formation (7,8,9,10), stimulation of acute phase protein synthesis (11) and inhibition of adipocyte lipoprotein lipase activity (12, 13). The diverse and pleiotropic function of IL-11 makes it an important haemopoietin molecule to study, especially at the level of its interaction with its receptor.

The structure of the IL-11 receptor is not well known. It is known that neutralizing antibodies to gp130 inhibit IL-11-dependent proliferation of TF-1 cells (14) and, hence, it is likely that gp130 forms part of the receptor.

Members of the haemopoietin receptor family generally comprise α- and β-chains (15,16,17). However, until the advent of the present invention, there was no information on the existence of IL-11 receptor chains. In work leading up to the present invention, the inventors developed a cloning procedure for haemopoietin receptors which does not require prior knowledge of their ligands. The cloning procedure has been successful in cloning the IL-11 receptor α-chain permitting, for the first time, a detailed molecular analysis of the IL-11 receptor. The present invention provides, therefore, a generalized method for cloning haemopoietin receptors and in particular component chains thereof which provides a basis for developing a range of agonists, antagonists, therapeutic and diagnostic agents based on the IL-11 receptor.

Accordingly, one aspect of the present invention provides a genetic molecule comprising a sequence of nucleotides encoding or complementary to a sequence encoding a haemopoietin receptor or a mutant, derivative, component, part, fragment, homologue, analogue or a peptide or polypeptide equivalent thereof wherein said receptor comprises an amino acid sequence set forth in SEQ ID NO: 1:

Trp-Ser-Xaa-Trp-Ser, wherein Xaa is any amino acid.

More particularly, the present invention contemplates a genetic molecule comprising a sequence of nucleotides encoding or complementary to a sequence encoding an IL-11 receptor or a mutant, derivative, component, part, fragment, homologue, analogue or a peptide or polypeptide equivalent thereof wherein said receptor comprises an amino acid sequence set forth in SEQ ID NO: 1:

Trp-Ser-Xaa-Trp-Ser, wherein Xaa is any amino acid.

Another aspect of the present invention contemplates a method of identifying and/or cloning a genetic sequence encoding or complementary to a sequence encoding a haemopoietin receptor and in particular an IL-11 receptor or a component or part thereof, said method comprising screening a source of genetic material with one or more degenerate oligonucleotides designed from the sequence of amino acids comprising the sequence set forth in SEQ ID NO: 1:

Trp-Ser-Xaa-Trp-Ser wherein Xaa is any amino acid residue.

The sequence defined in SEQ ID NO: 1 has been identified in both α and β chains of haemopoietin receptors and in particular IL-11 receptor. Accordingly, the method of the present invention is applicable to the cloning of genetic sequences encoding an α-chain, a β-chain or a combination of both α- and β-chains such as in a full length receptor.

Preferably, the genetic molecule is of mammalian origin such as but not limited to humans, livestock animals (e.g. sheep, cows, pigs, goats, horses), laboratory test animals (e.g. mice, rats, guinea pigs), companion animals (e.g. cats, dogs) or captive wild animals. Most preferred origins are from humans and murine species (e.g. mice). The source of genetic material may be a genomic library or a cDNA library obtained from mRNA from a particular cell type such as would not limit to liver cells, bone marrow cells, placenta cells and heptatoma cells. A cDNA library is preferred and may also be an expression library. Furthermore, for the generation of mutants the cDNA library may be prepared by high error rate polymerase chain reaction (PCR) resulting in a mutant library.

The term "screening" includes any convenient means to identify target clones. For example, colony hybridization may be employed with oligonucleotide probes or if an expression library is prepared, screening may be, for example, enzyme activity or antibody interactivity. Terms such as "components", "parts" or "fragments" include separately an α-chain and a β-chain or parts thereof. Preferably, the "components", "parts" and "fragments" are functional and more preferably a functional α- or β-chain.

The genetic molecule may be single or double stranded, linear or closed circle DNA (e.g. genomic DNA), cDNA or mRNA or combinations thereof. The genetic molecule may also include a vector such as an expression vector component to facilitate expression of the IL-11 receptor genetic sequence.

In a particular aspect, the genetic sequence encodes the α-chain of IL-11 receptor and in one preferred embodiment is murine IL-11 receptor α-chain encoded by a nucleotide sequence as set forth in SEQ ID NO: 2 or comprises an amino acid sequence as set forth in SEQ ID NO: 3, or comprises a part, derivative, fragment, portion, derivative, homologue, analogue or peptide equivalent thereof. In an alternative preferred embodiment, the genetic sequences encodes the α-chain of human IL-11 receptor and comprises the nucleotide sequence as set forth in SEQ ID NO: 4 or an amino acid sequence as set forth in SEQ ID NO: 5 or comprises a part, derivative, fragment, portion, derivative, homologue, analogue or peptide or polypeptide equivalent thereof. Accordingly, the genetic sequence may include a molecule capable of encoding a full length IL-11 receptor or a fragmented portion thereof such as an α-chain or a β-chain whether functional or not or may correspond to a portion thereof characterized by the amino acid sequence Trp-Ser-Xaa-Trp-Ser wherein Xaa is any amino acid residue. Additionally, the genetic sequence or part thereof may act as an antisense molecule or molecules to mRNA encoding the α- or β-chain of the IL-11 receptor. Such antisense molecules may be useful in genetic therapy or in the rational design of agonistic or antagonistic agents.

In a related embodiment, there is provided a genetic sequence which encodes an IL-11 receptor or a component, part or fragment thereof wherein said genetic sequence comprises a sequence of nucleotides to which SEQ ID NO: 2 or 4 may hybridise under low stringency conditions. In a further related embodiment, the genetic sequence is defined by the ability of an oligonucleotide selected from the following list to hybridise thereto:

5' (A/G)CTCCA(C/T)TC(A/G)CTCCA 3';   (SEQ ID NO:6)

5' (A/G)CTCCA(A/G)TC(A/G)CTCCA 3';   (SEQ ID NO:7)

5' (A/G)CTCCA(N)GC(C/T)CTCCA 3';   (SEQ ID NO:8)

5' (A/G)CTCCA(N)GG(A/G)CTCCA 3';   (SEQ ID NO:9)

5' (A/G)CTCCA(C/T)TT(A/G)CTCCA 3';   (SEQ ID NO:10)

or a complement sequence thereof or a combination thereof.

The present invention extends to the oligonucleotide defined by one of SEQ ID NOS: 1 to 6 and/or to labeled forms thereof or oligonucleotide stabilized to reduce nuclease-mediated action thereto.

For the purposes of defining the level of stringency, reference can conveniently be made to Sambrook et al (26) which is herein incorporated by reference where the washing steps at pages 9.52-9.57 are considered high stringency. A low stringency is defined herein as being in 0.1-0.5% w/v SDS at 37-45 C for 2-3 hours. Depending on the source and concentration of nucleic acid involved in the hybridisation, alternative conditions of stringency may be employed such as medium stringent conditions which are considered herein to be 0.25-0.5% w/v SDS at ≧45 C for 2-3 hours or high stringent conditions as disclosed by Sambrook et al (26).

The present invention is particularly useful for the cloning of haemopoietin receptor α- or β-chains, as exemplified by the cloning of the IL-11 receptor α-chain (IL-11rα). This is done, however, with the understanding that the present invention extends to a method for cloning all haemopoietin receptors including their α- or β-chains. Reference in the Examples to an α-chain is considered shorthand notation to the entire receptor or various parts thereof, including the α- or β-chain.

In a further embodiment, the genetic sequence is fused to a heterologous genetic sequence to thereby encode a fusion molecule with, for example, glutathione-S-transferase, a receptor or subunit thereof for IL-2, IL-3, IL-4, IL-5, IL-6, IL-7, IL-9, erythropoietin, thrombopoietin, growth hormone, prolactin, CNTF, G-CSF, GM-CSF, gp130, or the p40 subunit of IL-12.

The genetic molecule may be single or double stranded, linear or closed circle DNA (e.g. genomic DNA), cDNA or mRNA or combinations thereof such as in the form of DNA:RNA hybrids. The genetic molecule may also include a vector such as an expression vector component to facilitate expression of the IL-11 receptor or its components or parts. In a preferred embodiment, the genetic sequence encodes the α-chain of IL-11 having an amino acid sequence set forth in SEQ ID NO: 3 (murine) or SEQ ID NO: 5 (human) or comprises a part, derivative, fragment, portion, component, homologue or analogue of all or a portion thereof. Most preferably, the genetic sequence comprises a nucleotide sequence as set forth in SEQ ID NO: 2 (murine) or SEQ ID NO: 4 (human) or comprises a part, derivative, fragment, portion, component, homologue or analogue of all or part thereof.

The present invention further contemplates a kit useful for cloning a member of the haemopoietin receptor family or a component or part thereof, said kit comprising in compartmental form a first compartment adapted to contain at least one species of oligonucleotides having a nucleotide sequence based on the amino acid sequence SEQ ID NO: 1:

Trp-Ser-Xaa-Trp-Ser wherein Xaa is any amino acid residue, said kit further optionally comprising one or more other compartments adapted to contain one or more other species of oligonucleotide based on SEQ ID NO: 1 and/or reagents required for a hybridisation assay for haemopoietin receptor genetic sequences. The kit may also be packaged for same with instructions for use. Preferred oligonucleotides include but are not limited to SEQ ID NO: 6 to 10.

Yet another aspect of the present invention is directed to a recombinant polypeptide comprising a sequence of amino acids corresponding to all or part of a mammalian IL-11 receptor α-chain. Preferably, the mammal is a human or a murine species such as a mouse. The polypeptide may correspond to a full length α-chain or may be a functional part, fragment or derivative thereof or may be a part, fragment or derivative having agonistic or antagonistic properties. In a preferred embodiment the polypeptide comprises an amino acid sequence as substantially set forth in SEQ ID NO: 3 (murine) or SEQ ID NO: 5 (human) or having at least about 40%, more preferably at least about 50%, still more preferably at least about 65%, even still more preferably at least about 75-80% and yet even more preferably at least about 90-95% or greater similarity to the sequence set forth in SEQ ID NO: 3 or SEQ ID NO: 5.

The polypeptide may have additional amino acid sequences fused thereto including GST, another cytokine, a receptor component or gp130. It may be glycosylated or unglycosylated depending on the cell used to produce same. Accordingly, the polypeptide may be produced in a prokaryotic cell (e.g. *E. coli* or *Bacilli* sp) or in a eukaryotic cell (e.g. mammalian cells such as BA/F3 cells [18] yeast cells, insect cells).

Mutants and derivatives of the recombinant polypeptide haemopoietin receptor properties include amino acid substitutions, deletions and/or additions. Furthermore, amino acids may be replaced by other amino acids having like properties, such as hydrophobicity, hydrophilicity, electronegativity, bulky side chains, interactive and/or functional groups and so on.

Amino acid substitutions are typically of single residues; insertions usually will be of the order of about 1-10 amino acid residues; and deletions will range from about 1-20 residues. Deletions or insertions preferably are made in adjacent pairs, i.e: a deletion of 2 residues or insertion of 2 residues.

The amino acid variants referred to above may readily be made using peptide synthetic techniques well known in the art, such as solid phase peptide synthesis and the like, or by recombinant DNA manipulations. Techniques for making substitution mutations at predetermined sites in DNA having known sequence are well known, for example through M13 mutagenesis. The manipulation of DNA sequences to produce variant proteins which manifest as substitutional, insertional or deletional variants are well known in the art. Other examples of recombinant or synthetic mutants and derivatives of the recombinant haemopoietin receptor polypeptide of the present invention include single or multiple substitutions, deletions and/or additions to any molecule associated with the ligand such as carbohydrates, lipids and/or proteins or polypeptides. Naturally occurring or altered glycosylated forms of the subject ligand are particularly contemplated by the present invention.

Amino acid alterations to the subject polypeptide contemplated herein include insertions such as amino acid and/or carboxyl terminal fusions as well as intra-sequence insertions of single or multiple amino acids. Generally, insertions within the amino acid sequence will be smaller than amino or carboxyl terminal fusions, of the order of say 1 to 4 residues. Insertional amino acid sequence variants are those in which one or more amino acid residues are introduced into a predetermined site in the protein. Deletional variants are characterized by the removal of one or more amino acids from the sequence. Substitutional variants are those in which at least one residue in the sequence has been removed and a different residue inserted in its place. Such substitutions may be made in accordance with Table 1:

TABLE 1

| Original Residue | Exemplary Substitutions |
|---|---|
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

The terms "analogues" and "derivatives" also extend to any functional chemical equivalent of the ligand characterized by its increased stability and/or efficacy in vivo or in vitro. The terms "analogue" and "derivatives" further extend to any amino acid derivative of the ligand as described above.

Analogues of the haemopoietin polypeptide receptor contemplated herein include, but are not limited to, modifications to side chains, incorporation of unnatural amino acids and/or derivatising the molecule and the use of crosslinkers and other methods which impose conformational constraints on the peptides or their analogues. Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2, 4,6-trinitrobenzene sulphonic acid (TNBS); acylation of amino groups with succinic anhydride and tetrahydrophthalic anhydride; and pyridoxylation of lysine with pyridoxal-5'-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbomoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during protein synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids.

Crosslinkers can be used, for example, to stabilise 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides could be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogues by introducing covalent bonds such as forming an amide bond between the N and C termini, between two side chains or between a side chain and the N or C terminus.

The present invention, therefore, extends to peptides or polypeptides and amino acid and/or chemical analogues thereof having the identifying characteristics of the α-chain of IL-11 receptor.

Accordingly, reference herein to the α-chain of the IL-11 receptor or a polypeptide having IL-11 α-chain properties includes the naturally occurring molecule, recombinant, synthetic and analogue forms thereof and to any mutants, derivatives and human and non-human homologues thereof including amino acid and glycosylation variants.

The availability of recombinant IL-11 receptor α-chain and genetic sequences encoding same permits for the first time the development of a range of agonists, antagonists, therapeutics and diagnostics to treat a variety of conditions involving a deficiency of IL-11, an excess amount of IL-11 or aberrant effects of normal endogenous IL-11 levels. Accordingly, the present invention extends to these agonists, antagonists, therapeutics and diagnostics and to compositions, pharmaceutical compositions and agents comprising one or more of same.

The present invention further described by the following non-limiting Figures and/or Examples.

IN THE FIGURES:

FIG. 1 depicts the structure of the IL-11rα cDNA, showing the 5' and 3' untranslated regions (solid line) and the coding region containing the predicted signal sequence (▨), the mature extracellular domain (☐), transmembrane domain (▥) and cytoplasmic domain (▤). The size and extent of each of the IL-11rα cDNA clones that were sequenced completely are shown below.

FIGS. 2A-2C, joined at match lines A-A, B-B and C-C, show a comparison of Nr1 with other members of the haemopoietin receptor family; Amino acid sequence alignment of murine Nr1, the murine IL-6 receptor α-chain, the human CNTF receptor α-chain, the p40 subunit of human IL-12 and the murine GM-CSF receptor α-chain. Alignments were carried out by eye.

Figure 3:
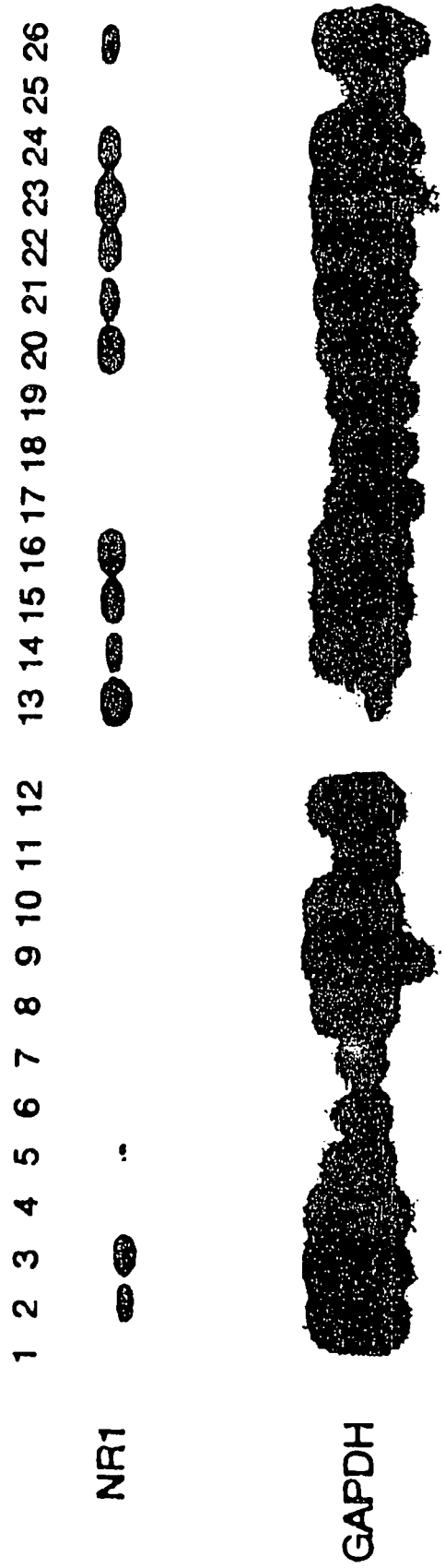

FIG. 3 is a photographic representation of reverse transcriptase polymerase chain analyses of Nr1 mRNA; Cytoplasmic RNA was prepared from the following sources; lane 2, 3T3-L1 cells; lane 3, BAd cells; lane 4, UMR-106 cells; lane 5, PC13 cells; lane 6, NFS-60 cells; lane 7, FDCP-1 cells; lane 8 32D cells; lane 9, D35 cells; lane 10, M1 cells; lane 11, J774 cells; lane 12 WEHI-3B D-cells; lane 13, human bone marrow; lane 14, mouse bone marrow; lane 15, mouse spleen; lane 16, mouse thymus; lane 17, mouse ovary; lane 18, mouse uterus; lane 19, mouse testis; lane 20, mouse epididymus; lane 21, mouse brain; lane 22, mouse heart; lane 23, mouse kidney; lane 24 mouse thigh muscle; lane 25; mouse liver and lane 26, mouse salivary gland. 1 µg of each RNA sample and a control containing no RNA (lane 1) was subject to reverse transcription, with an identical reaction performed in the absence of reverse transcriptase. 5% of first strand cDNA reaction was subjected to PCR with primers specific for Nr1 (upper panel) or the control GAPDH (lower panel). PCR products were resolved on a 1.0% w/v agarose gel, transferred to nitrocellulose and hybridised with internal oligonucleotides specific to GAPDH or Nr1.

FIGS. 4A-4D are graphical representations of scatchard analyses of saturation isotherms of IL-11 binding to various cell lines; (4A) parental Ba/F3 cells (●), Ba/F3 cells expressing Nr1 (○), Ba/F3 cells expressing Nr1 and the LIF receptor (■), (4B) Ba/F3 cells expressing the LIF receptor and gp130 (●), Ba/F3 cells expressing Nr1 and gp130 (■), Ba/F3 cells expressing the Nr1, LIF receptor and gp130 (○), (4C) parental M1 cells (●), M1 cells expressing Nr1 (○), and (4D) 3T3-L1 cells (■) were incubated with various concentrations of labeled IL-11 in the presence of absence of a 10-100-fold excess of unlabelled IL-11. After 18 hours incubation on ice, bound and free IL-11 were separated by centrifugation through foetal calf serum. Bound and free $^{125}$I-IL-11 was quantitated in a γ-counter and the data was depicted as a Scatchard transformation. In each case data were normalised for cell number and shown as binding to $10^6$ cells.

Figure 5:
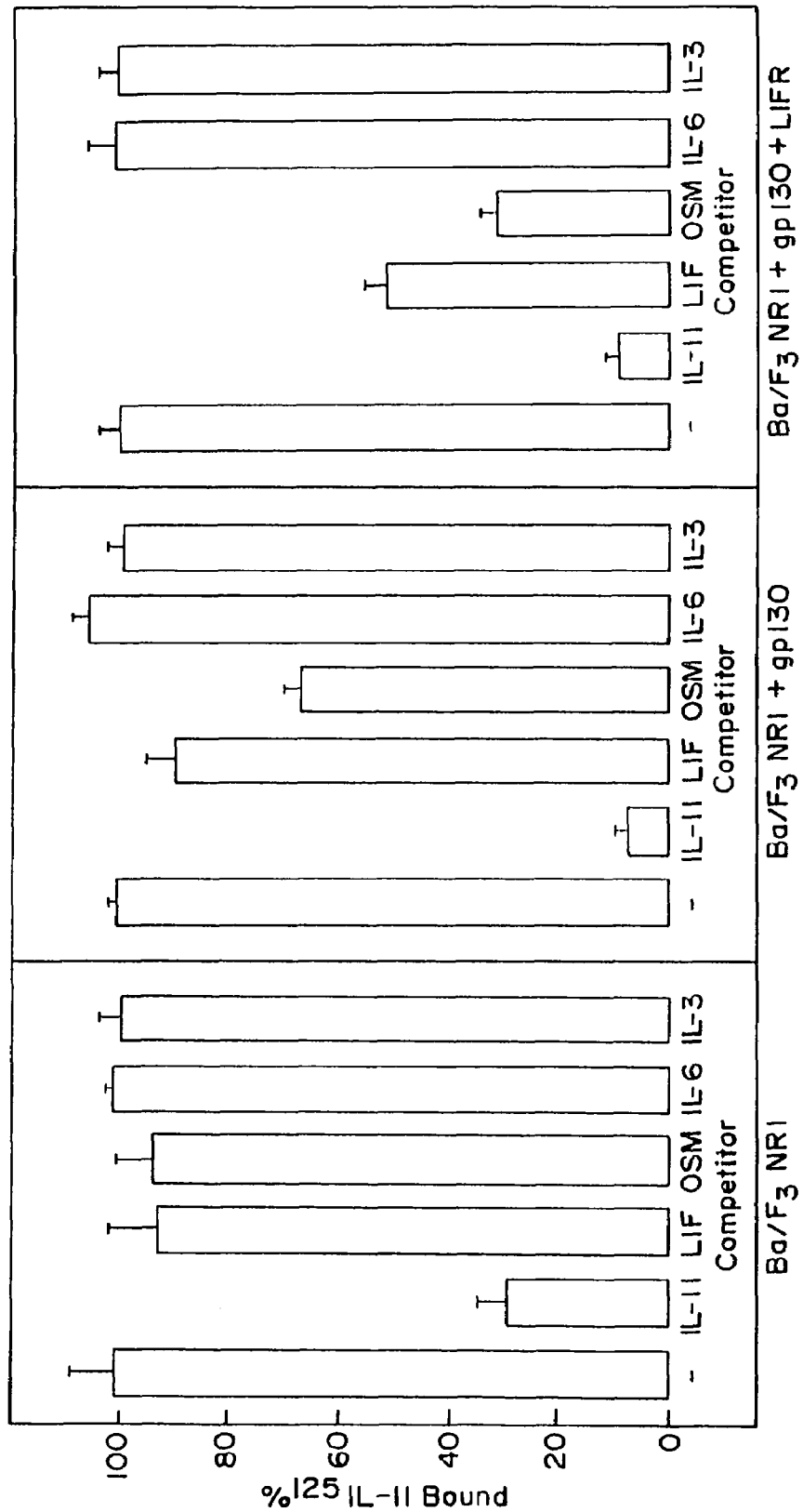

FIG. 5 shows the molecular specificity of IL-11 binding to various cell lines; Ba/F3 cells expressing the designated receptors were incubated in 100 µl of medium containing 60,000 cpm (Ba/F3 Nr1) or 6,000 cpm of $^{125}$I-IL-11 (Ba/F3 Nr1/gp130 and Ba/F3 Nr1/gp130/LIF receptor), in the presence or absence of 20 ng IL-11 or 200 ng of IL-6, LIF, OSM or IL-3. After 18 hours incubation on ice, bound and free IL-11 were separated by centrifugation through foetal calf serum. Bound and free $^{125}$I-IL-11 were quantitated in a γ-counter and the amount of binding was expressed as a percentage of that observed in the absence of competitor.

Figure 6:
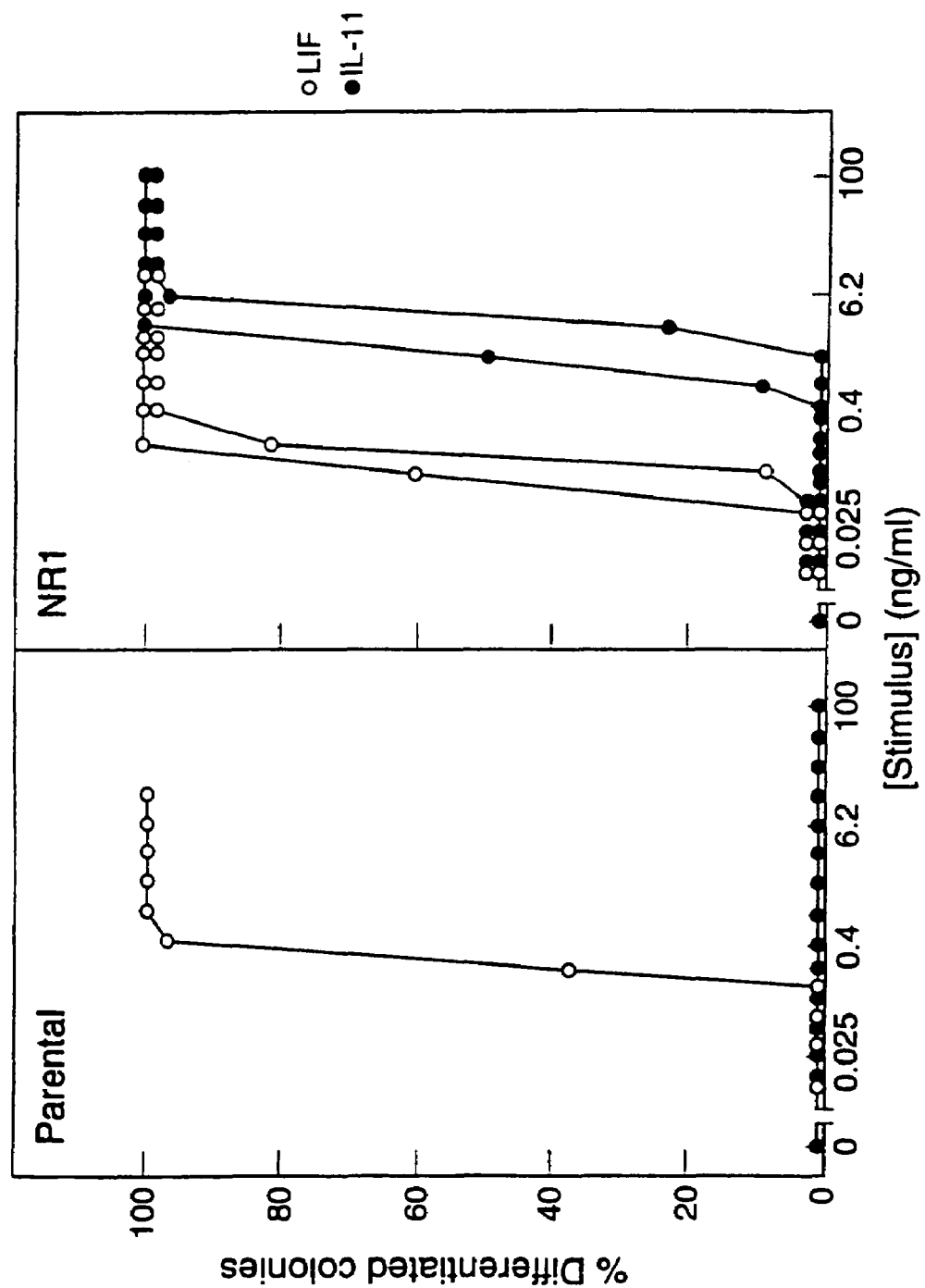

FIG. 6 shows differentiations of M1 cells expressing Nr1 in response to IL-11; 300 parental M1 cells (left panel) or M1 cells expressing Nr1 (right panel) were cultured in 1 ml of semi-solid agar with the designated concentration of LIF (○) or IL-11(●). After 7 days, the proportion of colonies containing differentiated cells were determined.

Figure 7:
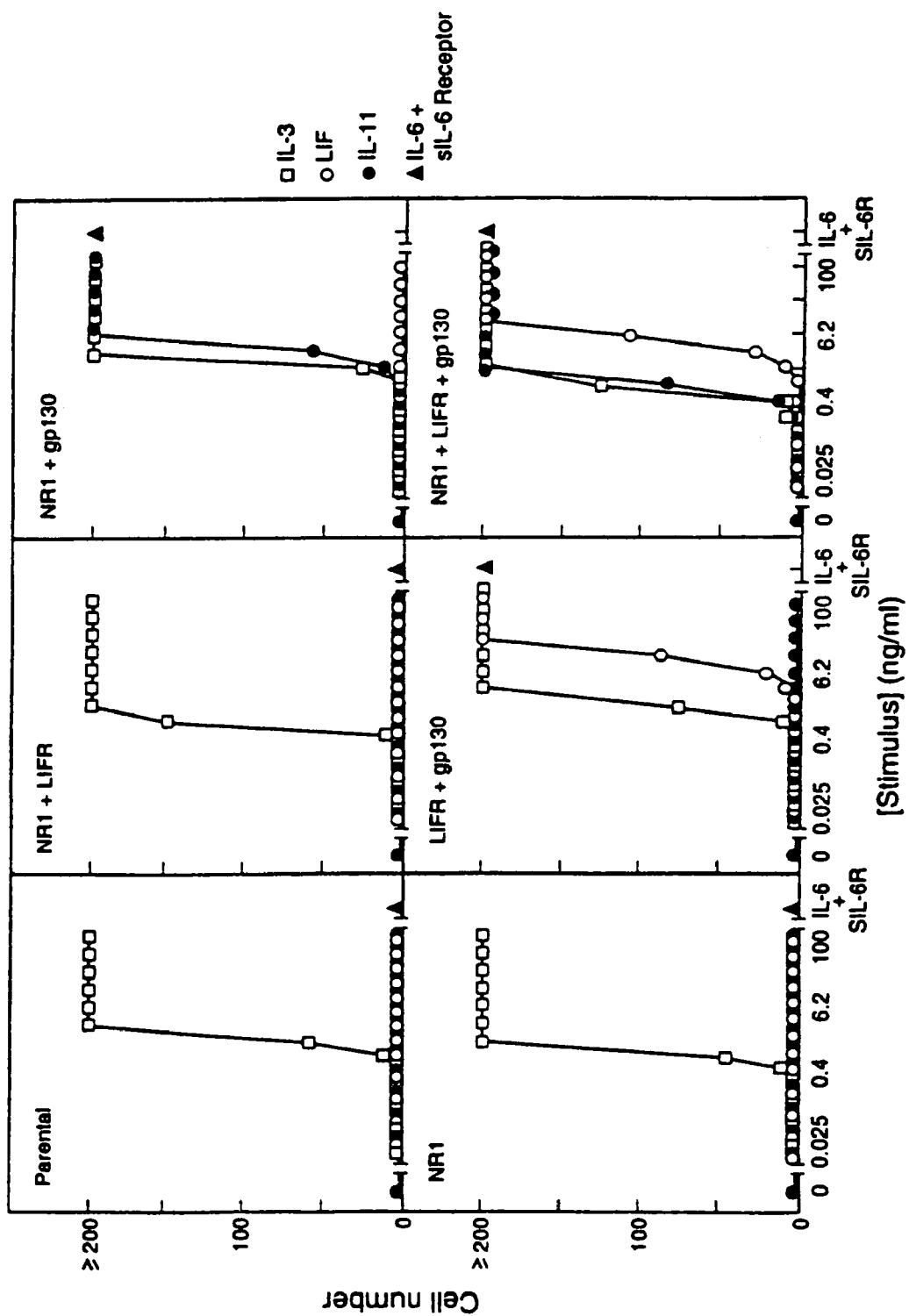

FIG. 7 shows factor dependent proliferation of Ba/F3 cells expressing various combinations of Nr1, gp130 and the LIF receptor; Parental Ba/F3 cells, Ba/F3 cells expressing Nr1, Ba/F3 cells expressing the Nr1 and the LIF receptor, Ba/F3 cells expressing LIF receptor and gp130, Ba/F3 cells expressing Nr1 and gp130 and Ba/F3 cells expressing Nr1, the LIF receptor and gp130 were incubated at 200 cells per well in a volume of 15 µl, with the designated concentrations of IL-11 (●), IL-3(☐) or LIF(○), or with 3 µg/ml IL-6 and 500 ng/ml soluble IL-6 receptor α-chain (▲). After 48 hours the numbers of viable cells were counted.

FIGS. 8A-8D, joined at match lines A-A, B-B, C-C and D-D provide a representation of the composite nucleotide sequence and the predicted amino acid sequence of the human IL-11 receptor a chain. The predicted amino acid sequence is displayed using the conventional single letter code.

FIG. 9 is a representation of a comparison of the predicted amino acid sequence of the human (H) and the murine (M) IL-11 receptor a chain. The asterisk symbol indicates identity. The hatch (#) marks represent gaps introduced to improve the alignment.

FIGS. 10A-10B are photographic representations of a Southern blot demonstrating cross-species hybridisation of (10A) murine IL-11 receptor a chain cDNA probe (445 bp Sph I/Sac I fragment) and (10B) of human IL-11 receptor a chain cDNA probe (560 bp Pst I/Xba I fragment from clone #17.1) to human (H) and to murine (M) genomic DNA digested with Hind III. Nylon membrane processed under conditions of high stringency (0.2X SSC, 0.1% w/v SDS, 65° C.). Exposure was for 16 hours at −70° C. using intensifying screens.

Figure 11:
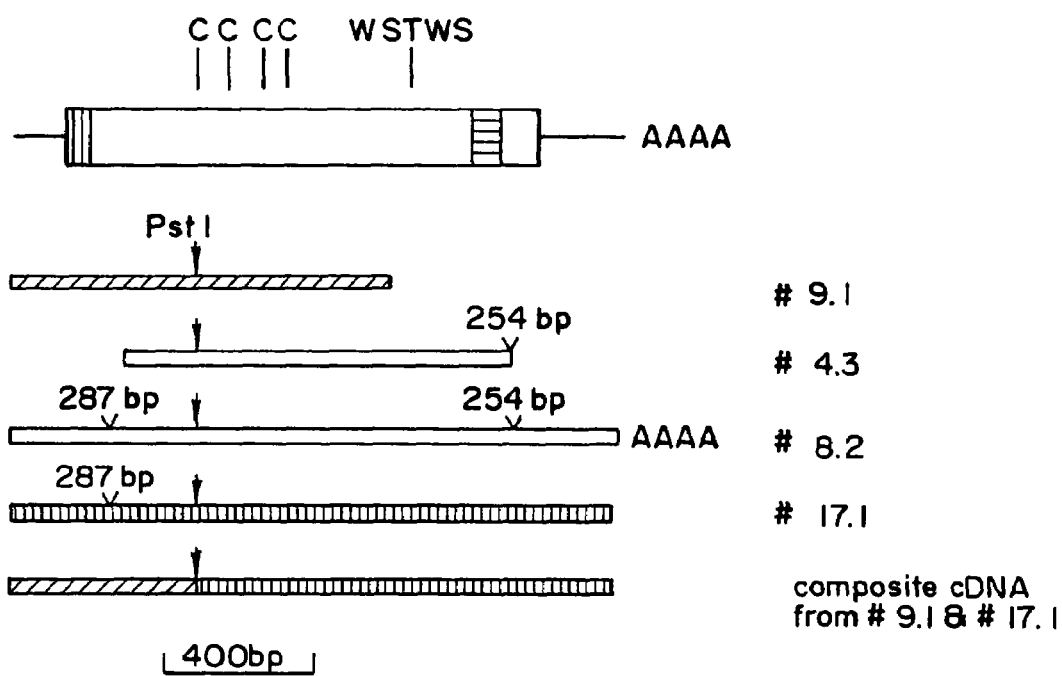

FIG. 11 is a diagrammatic representation of structure of the human IL-11rα cDNA, displaying the 5' and 3' untranslated region (solid line) and the coding region containing the signal sequence (▥), the extracellular domain (☐), the transmembrane region (▤), the cytoplasmic portion (■) and the poly A tail (AAAA). The approximate position of the conserved cysteine residues (C) and the WSTWS motif is indicated. The size and extent of the four cDNA clones selected for analysis is shown below. The approximate positions of the introns is indicated (V) as is their size in bp. The length of the clones is depicted without the introns. The composite cDNA was obtained from clines #9.1 and #17.1 by ligation at the indicated Pst I site (arrow) and used for expression studies.

FIG. 12 is a diagrammatic representation of scatchard analyses of saturation isotherms of human IL-11 binding to M1 cells manipuated to express human IL-11rα ( ), M1 cells expressing the murine IL-11rα(●) and parental M1 cells (○).

Cells were incubated with various concentrations of labeled IL-11 in the presence of 10-100-fold excess of unlabelled IL-11. After 18 hours incubation on ice, bound and free IL-11 were separated by centrifugation through FCS. Bound and free labeled IL-11 was quantitated n a γ counter and the data was depicted as a Scatchard transformation. In each case data were normalised for cell number and shown as binding to $10^6$ cells. The amount of non-specific binding was between 0.1 and 1% of the total labeled IL-11 added. High-affinity binding was seen for M1 cells expressing human IL-11rα ($K_d$=250 pM) and urine IL-11rα ($K_d$=275 pM). Parental M1 cells did not display any specific binding.

FIGS. 13A-13D are photographic representations showing morphology of parental M1 cells and M1 cells manipulated to express the human IL-11 receptor a chain (M1/hIL-11rα) and in response to human IL-11 (1000 U/ml) and murine LIF (1000 U/ml). Cell morphology was examined after 5 days of incubation. FIGS. 13A-13C show parental M1 cells with: normal saline (Panel a), LIF (Panel b) and IL-11 (Panel c). FIG. 13D is representative of M1/hIL-11rα cells stimulated with IL-11 (X 400).

Figure 14:
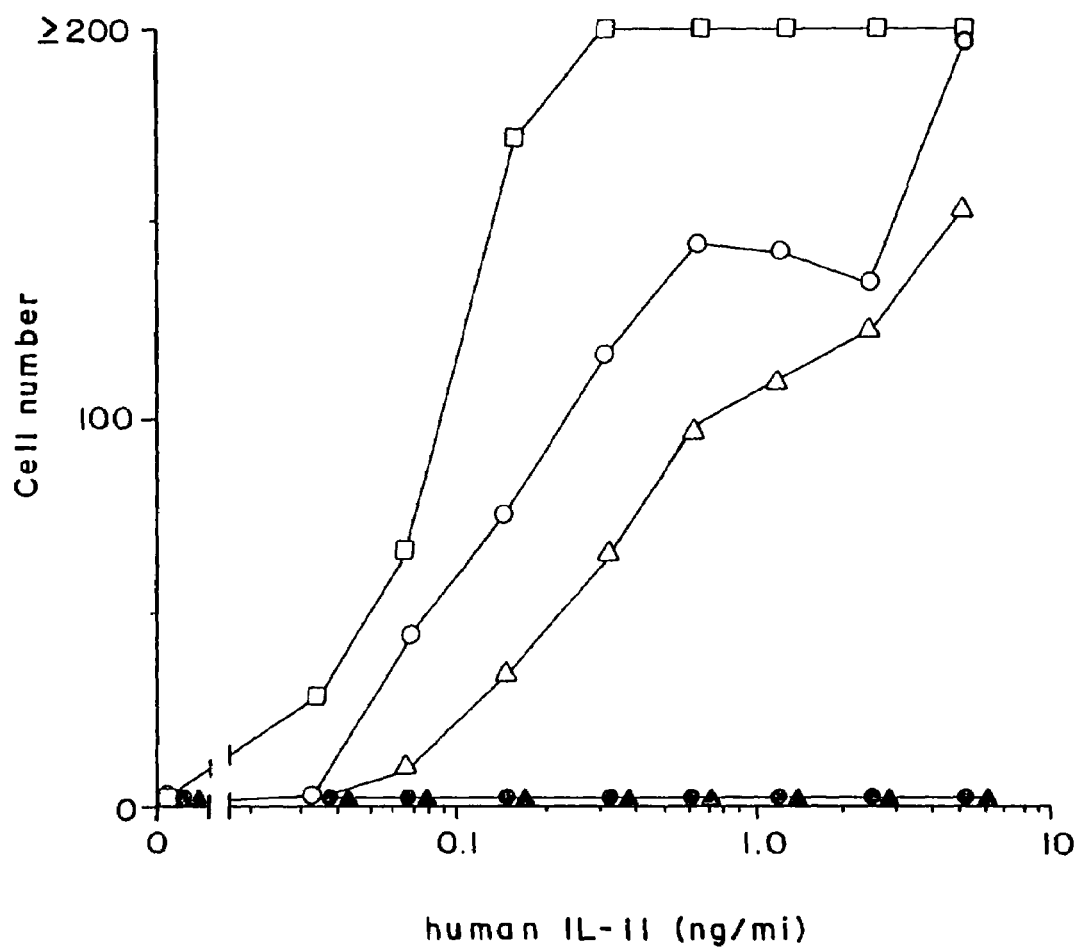

FIG. 14 is a graphical representation showing proliferation of parental Ba/F3 cells (▲), Ba/F3 cells manipulated to express the human IL-11 receptor a chain (Ba/F3+hIL-11rα) and Ba/F3 manipulated to express human IL-11 receptor a chain along with human gp130 (Ba/F3+hIL-11rα+gp130). Three clonal cell lines (Ba/F3+hIL-11rα) were established (represented by ●) that were unresponsive. Following the expression of the human gp130 molecule, all cell lines were IL-11 responsive (open symbols). Series dilutions of human IL-11 are shown. The results are means of triplicates from two experiments. All cells proliferated in IL-3.

The following single and three letter abbreviations for amino acid residues are used in the specification:

| Amino Acid | Three-letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidme | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valme | Val | V |
| Any residue | Xaa | X |

The following abbreviations are adopted in the subject specification:
IL-11: Interleukin 11
IL-11r: IL-11 receptor
IL-11rα: IL-11 receptor α-chain
D: Domain
SD: Sub-domain
Nr1: IL-11r

EXAMPLE 1

Library Screening

Commercial adult mouse liver cDNA libraries cloned into λgt10 and λZAP (Clonetech, CA, USA and Stratagene, CA, USA) were used to infect *Escherichia coli* of the strain LE392. Infected bacteria were grown on twenty 150 mm plates of agar, to give approximately 50,000 plaques per plate. Plaques were then transferred to duplicate 150 mm diameter nylon membranes (Colony/Plaque Screen™, NEN Research Products, MA, USA), bacteria were lysed and the DNA was fixed by autoclaving at 100° C. for 1 min with dry exhaust. The filters were rinsed twice in 0.1% w/v sodium dodecyl sulfate (SDS), 0.1×SSC(SSC is 150 mM sodium chloride, 15 mM sodium citrate dihydrate) at room temperature and pre-hybridised overnight at 37° C. in 6×SSC containing 2 mg/ml bovine serum albumin, 2 mg/ml Ficoll, 2 mg/ml polyvinyl-pyrrolidone, 100 μM ATP, 10 μg/ml tRNA, 2 mM sodium pyrophosphate, 2 mg/ml salmon sperm DNA, 0.1% NP-40 and 200 μg/ml sodium azide. The pre-hybridisation buffer was removed. An amount of 1.2 μg of the degenerate oligo-nucleotides for hybridisation (HYB1, HYB2 and HYB3; Table 1) were phosphorylated with T4 polynucleotide kinase using 960 μCi of $γ^{32}P$-ATP (Bresatec, S.A., Australia). Unincorporated ATP was separated from the labeled oligonucleotide using a pre-packed gel filtration column (NAP-S; Pharmacia, Uppsala, SWEDEN). Filters were hybridised overnight at 37° C. in 80 ml of the prehybridisation buffer containing 0.1% w/v SDS, rather than NP40, and $10^6$-$10^7$ cpm/ml of labeled oligonucleotide. Filters were briefly rinsed twice at room temperature in 6×SSC, 0.1% v/v SDS, twice for 30 min at 45° C. in a shaking waterbath containing 1.5 l of the same buffer and then briefly in 6×SSC at room temperature. Filters were then blotted dry and exposed to autoradiographic film at –70° C. using intensifying screens, for 7-14 days prior to development.

Plaques that appeared positive on orientated duplicate filters were picked, eluted in 1 ml of 100 mM NaCl, 10 mM $MgCl_2$, 10 mM Tris.HCl pH7.4 containing 0.5% w/v gelatin and 0.5% v/v chloroform and stored at 4° C. After 2 days LE392 cells were infected with the eluate from the primary plugs and replated for the secondary screen. This process was repeated until hybridising plaques were pure.

EXAMPLE 2

Analyses of Positive Plaques

DNA was prepared from positive plaques using Promega Magic Lambda DNA columns (Promega Corporation, WI, USA) according to the manufacturer's instructions. An amount of 100 ng of DNA from each positive bacteriophage was sequenced using a fmol sequencing kit (Promega Corporation, WI, USA) with the $^{33}P$-labeled oligonucleotide primers gt10for, gt10rev and either HYB1, HYB2 or HYB3. The products were resolved on a 6% w/v polyacrylamide gel and the sequence of each clone was analysed using the Blast database comparison programs and the translation function of the Wisconsin suite of programs.

The sequence of one clone (Nr1-AZ-36) contained motifs characteristic of the haemopoietin receptor family. Two oligonucleotides, #26 and #60 (nucleotides 946-970 and 1005-

1034; FIG. 1; Table 2), were designed from this sequence and used rescreen the primary filters from the original liver library and two other adult liver cDNA libraries. The initially isolated cDNA clone, Nr1-AZ-36, and four other cDNA clones (Nr1-30.2, 30.3, 30.4 and 30.17) were sequenced completely, on both strands, using the dideoxy method (18) with the Pharmacia T7 polymerase sequencing kit (Pharmacia, Uppsala, SWEDEN). The sequence of the new receptor was compared to the EMBL and Genbank database using the FASTA program. Alignments with known cytokine receptors were carried out by eye.

An alternative, quicker method for the analysis of positive plaques identified using degenerate oligonucleotides to the WSXWS motif.

Primary positive plaques are identified and picked.

5 µl of primary plaque eluate was used in a polymerase chain reaction containing the following: 5 µl 10×PCR buffer with Mg (Boehringer Mannheim), 1 µl 10 mM dATP, dCTP, dGTP and dTTP (Promega Corp), 2.5 µl of each primer at 100 µg/ml and 0.5 µl of Taq polymerase (Boehringer Mannheim). The primers utilised were those WSXWS primers used in hybridisation in combination with primers specific to the λ-bacteriophage in which the library was cloned. PCR was carried in a Perkin Elmer 9600 machine using the following protocol: 96° C. for 2 min, 25 cycles of 96° C. for 30 sec, 55° C. for 30 sec and 72° C. for 2 min, 4° C. indefinitely.

20 µl of the PCR was electrophoresed on a 1% w/v agarose gel in TAE. Any products were isolated using GeneClean reagent and sequenced either using $^{33}$P-labeled WSXWS primers with the fmol sequencing kit (Promega Corp) or unlabelled WSXWS primers and fluoresceinated dideoxy nucleotides with an automated sequencer. The sequence is then used to check for motifs common to receptors of the haemopoietin family.

EXAMPLE 3

Reverse Transcriptase Polymerase Chain Reaction

First strand cDNA synthesis was performed on 1 µg of polyA+ cytoplasmic RNA. Reverse transcription was carried out at 42° C. for 60 min in 20 µl of 50 mM Tris.HCl pH8.3, 20 mM KCl, 10 mM $MgCl_2$, 5 mM dithiothreitol, 1 mM of each dNTP, 20 µg/ml oligo $(dT)_{15}$ and 12.5 units of AMV reverse transcriptase (Boehringer Mannheim GmbH, Mannheim, Germany). Control reactions were performed for each RNA sample under identical conditions except that reverse transcriptase was omitted from the reaction. The reverse transcription reaction mixture was diluted to 100 µl with water and 5 µl was used for each PCR reaction. PCR reactions were carried out in 50 µl of reaction buffer (Boehringer Mannheim GmbH, Mannheim, Germany) containing 200 µM of each dNTP, 1 µM of each primer and 2.5 U of Taq polymerase (Boehringer Mannheim GmbH, Mannheim, Germany). The primers used for amplification of IL-11 receptor α-chain (Nr1) cDNA were, from homologY with other members of the haemopoietin receptor family, predicted to span at least one intron. These oligonucleotides were #449 and #285 (nucleotides 133-156 and 677-661; FIG. 1, Table 2), while for amplification of GAPDH cDNA primers #495 and #496 were used (Table 2). PCR was performed for 30 cycles at 94° C. for 2 min, at 60° C. for 2 min and at 72° C. for 3 min in a Perkin Elmer Cetus Thermal cycler (Perkin Elmer Cetus, CA, USA). An aliquot of the reaction mixture was electrophoresed on a 1.0% w/v agarose gel and DNA was transferred to a zetaprobe membrane. Southern blots were performed as described by Reed and Mann (19). Hybridisation was carried out with

TABLE 2

SEQUENCE OF OLIGONUCLEOTIDES

| Oligonucleotide | Sequence | SEQ ID NO: |
|---|---|---|
| HYB1 | 5' (A/G)CTCCA(C/T)TC(A/G)CTCCA 3' | SEQ ID NO:6 |
| HYB2 | 5' (A/G)CTCCA(A/G)TC(A/G)CTCCA 3' | SEQ ID NO:7 |
| HYB3 | 5' (A/G)CTCCA(N)GC(C/T)CTCCA 3' | SEQ ID NO:8 |
| #26 | 5' TGGTCCACGGTGGAGCCCATTGGCT 3' | SEQ ID NO:11 |
| #60 | 5' CCACACGCGGTACGAGTCAGTGCCAGGGAC 3' | SEQ ID NO:12 |
| gt10for | 5' AGCAAGTTCAGCCTGGTTAAG 3' | SEQ ID NO:13 |
| gt10rev | 5' CTTATGAGTATTTCTTCCAGGGTA 3' | SEQ ID NO:14 |
| #495 | 5' CCCTTCATTGACCTCAACTACATG 3' | SEQ ID NO:15 |
| #496 | 5' CATGCCAGTGAGCTTCCCGTTCAG 3' | SEQ ID NO:16 |
| #449 | 5' GGGTCCTCCAGGGGTCCAGTATGG 3' | SEQ ID NO:17 |
| #285 | 5' GGAGGCCTCCAGAGGGT 3' | SEQ ID NO:18 |
| #489 | 5' CTCCTGTACTTGGAGTCCAGG 3' | SEQ ID NO:19 |
| #741 | 5' GGAAAGCTGTGGCGTGATGGCCGTGGGCA 3' | SEQ ID NO:20 |
| 30f1 | 5' GGGCGGAGGCCGCTGGCGGGCG 3' | SEQ ID NO:21 |
| 30r1 | 5' TTATCAGCTGAAGTTCTCTGGGG 3' | SEQ ID NO:22 | end-labeled oligonucleotides (#489 for the IL-11 receptor α-chain and #741 for GAPDH; Table 2).

EXAMPLE 4

Expression Constructs

Nr1-30.3 was used in a PCR with primers 30f1 and 30r1 (Table 2) to generate a cDNA that contained little 5' or 3' untranslated region. The PCR product was cloned into the BstX I site of pEF-BOS (21) using BstX I adaptors (Invitrogen, CA, USA). The cDNA insert was sequenced on both strands. cDNAs encoding the human LIF receptor and mouse gp130 were also subcloned into pEF-BOS. Receptor cDNAs in pEF-BOS were linearized with Aat II prior to transfection. pBluescript derivatives containing cDNAs encoding the selectable markers puromycin transferase (pPGKpuropA) and neomycin transferase (pPGKneopA) transcribed from a PGK promoter and with the β-globin 3'-untranslated region were linearised with Sca I.

EXAMPLE 5

Cell Transfection

Cells were stably transfected by electroporation. Briefly, cells were washed twice in ice cold PBS and resuspended in PBS at $5 \times 10^6$ per ml. An amount of $4 \times 10^6$ cells was aliquoted into 0.4 mm electroporation cuvettes with 20 μg of pEF-BOS with or without Nr1, gp130 or the LIF receptor cloned into the BstX I site and 2 μg of the selectable markers pPGKpuro or pPGKneo. DNA and cells were incubated for 10 minutes on ice and electroporated at 270 V and 960 μF in a Bio-Rad Gene Pulser (Bio-Rad Laboratories, CA, USA). The cells were mixed with 1 ml of culture medium, centrifuged through 3 ml of FCS and resuspended in 100 ml of culture medium. Cells were than aliquoted into four 24 well dishes. After two days, selection was commenced by the addition of geneticin to a concentration of 1.2 mg/ml, of puromycin to a concentration of 40 μg/ml for M1 cells and 5 μg/ml for Ba/F3 cells. After 10-14 days, clones of proliferating cells were transferred to flasks and, after expansion, tested for receptor expression.

EXAMPLE 6

Cytokines

Murine IL-3 and IL-11 were purchased from PeproTech (PeproTech, NJ, USA), human LIF and human OSM were produced using the pGEX system, essentially as described (25).

EXAMPLE 7

Biological Assays

The proliferation of Ba/F3 cells in response to cytokines was measured in Lux60 microwell HL-A plate (Nunc Inc., IL, USA). Cells were washed three times in DME containing 20% v/v new born calf serum and resuspended at a concentration of $2 \times 10^4$ cells per ml in the same medium. Aliquots of 10 μl of the cell suspension were placed in the culture wells with 5 μl of serial dilutions of purified recombinant IL-3, IL-11 or LIF, or IL-6 at 3 μg/ml and soluble IL-6 receptor α-chain at 500 ng/ml. After 2 days of incubation at 37° C. in a fully humidified incubator containing 10% V/V $CO_2$ in air, viable cells were counted using an inverted microscope.

In order to assay the differentiation of M1 cells in response to cytokines, 300 cells were cultured in 35 mm Petri dishes containing 1 ml of DME supplemented with 20% v/v FCS, 0.3% w/v agar and 0.1 ml of serial dilutions of IL-6, IL-11, LIF or OSM. After 7 days culture at 37° C. in a fully humidified atmosphere, containing 10% v/v $CO_2$ in air, colonies of M1 cells were counted and classified as differentiated if they contained dispersed cells or a corona of dispersed cells around a tightly packed centre.

EXAMPLE 8

Binding Studies with IL-11

IL-11 was dissolved at a concentration of 100 μg/ml in 50 mM sodium phosphate, 150 mM NaCl (PBS), 0.02% v/v Tween 20 and 0.02% w/v sodium azide at pH 7.4. IL-11 was radio-iodinated according to the method of Bolton and Hunter (24). Briefly, 2 μg of IL-11 was incubated with 2 mCi of monoiodinated Bolton-Hunter reagent (New England Nuclear, MA, USA) at room temperature in 20 μl of 150 mM sodium borate pH 8.5. After two hours the reaction was quenched with 100 μl of 1M glycine in the same buffer and the labeled protein was separated from unincorporated Bolton-Hunter reagent using a pre-packed Sephadex G-25 column (PD-10; Pharmacia, Uppsala, Sweden) equilibrated in PBS containing 0.02% v/v Tween 20 and 0.02% w/v sodium azide. Prior to use the $^{125}$I-IL-11 was diluted 10-fold with 50 mM Tris HCl pH 7.5, containing 0.02% v/v Tween 20 and 0.02% w/v sodium azide and applied to a 250 μl column of CM-Sepharose CL-4B (Pharmacia, Uppsala, SWEDEN) equilibrated in the same buffer. The column was washed with 5 ml of equilibration buffer and eluted with sequential 5 ml aliquots of DME containing 10% v/v FCS. At this stage the $^{125}$I was greater than 95% precipitable with cold trichloroacetic acid. The bindability of the $^{125}$I-IL-11 preparation was assessed as previously described (21) and was approximately 80%. The specific radioactivity of the $^{125}$I-IL-11 was approximately 130,000 cpm/ng and was determined by self-displacement analysis (22).

Binding studies were performed essentially as previously described (22). Briefly, $5 \times 10^5$-$1.5 \times 10^7$ cells in 40 μl RPMI-1640 medium containing 20 mM Hepes pH 7.4 and 10% v/v foetal calf serum (RHF), were incubated overnight on ice, with between $5 \times 10^3$ and $2 \times 10^6$ cpm of $^{125}$I-IL-11, with or without a 100-fold excess of unlabelled IL-11. In other experiments receptors were saturated with constant amount of $^{125}$I-IL-11 and increasing amounts of unlabelled IL-11 or unlabelled IL-3, IL-6, LIF, OSM or G-CSF. Cell associated and free $^{125}$I-IL-11 were separated by rapid centrifugation through 180 μl of foetal calf serum and quantitated in a γ-counter.

EXAMPLE 9

Cloning Cytokine Receptors on the Basis of Sequence Similarity

Members of the haemopoietin receptor family exhibit a relatively low level of sequence similarity. One of the features of receptors in this family is the five amino acid motif Trp-Ser-Xaa-Trp-Ser (WSXWS) (15, 16, 17). In an attempt to clone novel haemopoietin receptors, $10^6$ plaques from an adult mouse liver cDNA library were screened with degenerate oligonucleotides corresponding to the WSXSW motif. λ-bacteriophage plaques that appeared positive on the duplicate primary filters were picked, eluted and isolated by two subsequent rounds of plaque enrichment. DNA from pure hybridising plaques was then sequenced.

The utility of this technique was demonstrated by the identification of several cDNAs encoding the murine LIF receptor, IL-7 receptor, gp130 and a novel sequence that appeared related to members of the haemopoietin receptor family which is termed herein "Nr1". The cDNA (Nr1-AZ-36) encoding this novel receptor was sequenced fully and although it contained a polyadenylation signal and an extensive poly-A tail, it was clearly truncated at the 5' end (FIG. 1).

EXAMPLE 10

Isolation of Full Length Nr1 cDNA and Characterisation of the Novel Cytokine Receptor To isolate a full length Nr1 cDNA, the original library and a second adult mouse liver cDNA library were screened with oligonucleotides (#26 and #60; Table 2) designed from the 5' end of clone Nr1-AZ-36. Eight cDNA clones were isolated and four were sequenced completely (FIG. 1). Analyses of the cDNA sequences revealed an open reading frame of 1296 bp which encoded a protein of 432 amino acids in length. The predicted primary sequence included a potential hydrophobic leader sequence (residues 1-23), extracellular domain with two potential N-linked glycosylation sites (residues 24-367), transmembrane domain (residues 368-393) and short cytoplasmic tail (residues 394-432). The core molecular weight of the mature receptor has been initially estimated to be approximately 36,000 daltons.

The extracellular domain contained residues characteristic of a classical haemopoietin domain (D200; 15) (FIGS. 1 and 2A-2C), including proline residues preceding each 100 amino acid sub domain (SD100), four conserved cysteine residues, a series of polar and hydrophobic residues, and a WSXWS motif. The haemopoietin receptor domain of the new receptor was preceded by an 87 amino acid immunoglobulin-like domain and followed by 37 amino acids before the transmembrane domain. Regarding its overall structure and its primary sequence (FIGS. 2A-2C), the new receptor was most similar to the IL-6 receptor α-chain (24% amino acid identity), the CNTF receptor α-chain (22% amino acid identity) and the p40 subunit of IL-12 (16% amino acid identity).

EXAMPLE 11

Expression OF Nr1 mRNA

The distribution of Nr1 mRNA expression was analysed by Northern blot and reverse transcriptase polymerase chain reaction (RT-PCR). Among a survey of polyadenylated RNA from 15 primary tissue samples and 17 cell lines, only RNA from the pre-adipocyte cell line 3T3-L1, yielded a detectable hybridising band of approximately 2.0 kb in length on a Northern blot. This compares to a length of approximately 1650 bp for the longest Nr1 cDNA isolated and suggests that this clone may not be complete at the 5' end.

The low abundance of the Nr1 mRNA suggested from Northern analyses prompted the use of RT-PCR as a more sensitive means of detection. All samples contained GAPDH mRNA as judged by RT-PCR (FIG. 3), however only 3T3-L1 cells, the stromal line BAd, the embryonic carcinoma cell line PC13 and the factor dependent haemopoietin cell lines FDCP-1 and D35 expressed Nr1 mRNA (FIG. 3). A wide range of primary tissues were also positive (FIG. 3) including the haemopoietin tissues bone marrow, spleen and thymus as well as the liver, brain, heart, kidney, muscle and salivary gland. In mRNA samples from several cell lines and tissues transcripts for Nr1 could not be detected. Such negative results need to be confirmed using a more quantitative approach to mRNA analysis. In control experiments, PCR was performed on mRNA that had not been subjected to reverse transcription. In none of these samples was a Nr1 product detected.

EXAMPLE 12

Nr1 is a Low Affinity Receptor for IL-11 and Interacts with gp130 to Generate a High Affinity IL-11 Receptor Given its sequence similarity with the IL-6 and CNTF receptor α-chains and its expression in 3T3-L1-cells, it was reasoned that Nr1 might be a receptor α-chain which interacts with gp130 and/or the LIF receptor to generate a high affinity receptor capable of signal transduction. Since no receptor α-chains, similar in structure to the IL-6 receptor α-chain, have been described for LIF, OSM and IL-11, these cytokines represent attractive candidates for the cognate ligand of Nr1.

To test whether LIF, OSM or IL-11 bound to the new receptor, the factor-dependent haemopoietin cell line Ba/F3 and the mouse leukaemic cell line M1 were stably transfected with the vector pEF-BOS containing the cDNA encoding Nr1. Parental M1 cells express the LIF receptor and gp130 and, therefore, bound $^{125}$I-LIF and $^{125}$I-OSM. Expression of Nr1 in M1 cells did not result in altered binding of either $^{125}$I-LIF or $^{125}$I-OSM. In contrast, Ba/F3 cells expressed neither the LIF receptor nor gp130 and no binding of $^{125}$I-LIF and $^{125}$I-OSM was observed on either parental Ba/F3 cells or cells expressing Nr1.

Figure 4:
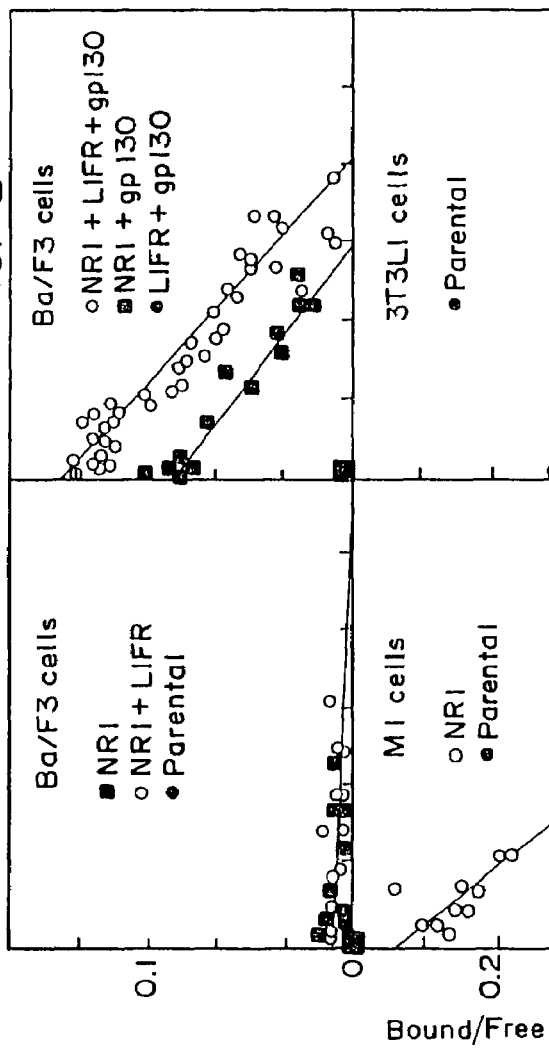

No binding of $^{125}$I-IL-11 could be detected on parental M1 or Ba/F3 cells (FIGS. 4A & C). Strikingly, however, expression of Nr1 in each cell type resulted in the ability to bind $^{125}$I-IL-11 which suggested that Nr1 might be the α-chain of the IL-11 receptor. Scatchard transformation of the saturation binding isotherms revealed that the affinity of IL-11 for its receptor differed between the two cell types (FIG. 4A versus 4C). Binding of $^{125}$I-IL-11 to Ba/F3 cells expressing Nr1 was of very low affinity. The apparent equilibrium dissociation constant ($K_D$) for this interaction was estimated to be approximately 10 pM and cells expressed an average of between 2,000 and 8,000 receptors at their surface (FIG. 4A). M1 cells transfected with a Nr1 cDNA expressed a similar number of IL-11 receptors (FIG. 4C), however, the affinity of the interaction was higher ($K_D$=400-800 pM). The IL-11 receptors expressed on M1 cells transfected with Nr1 were similar in affinity to the receptors expressed naturally on 3T3-L1 cells (FIG. 4D).

One explanation for the generation of low affinity or high affinity receptors according to the cell type in which Nr1 is expressed, is that Nr1 itself has an intrinsically low affinity for IL-11, but M1 cells express an excess of an additional receptor component required for the generation of a high affinity complex. Indirect evidence exists for the role of gp130 in IL-11 receptor signal transduction, since neutralising antibodies to gp130 inhibited IL-11 induced proliferation of TF-1 cells. In order to test this proposition directly, gp130 and/or the LIF receptor were expressed in parental Ba/F3 cells or in Ba/F3 cells expressing Nr1.

Parental Ba/F3 cells and Ba/F3 cells expressing gp130 and the LIF receptor, alone or in combination did not bind IL-11 (FIGS. 4A and B). Ba/F3 cells expressing Nr1 and the LIF receptor, bound IL-11 with a very low affinity that was indistinguishable from cells expressing IL-11 receptor α-chain alone (FIG. 4A). In contrast, when gp130 and Nr1 were co-expressed in Ba/F3 cells, high affinity receptors for IL-11 were generated (FIG. 4B). The affinity of these receptors was similar to that of receptors expressed by 3T3-L1 cells and M1 cells expressing IL-11 receptor α-chain (FIG. 4B-D). Expression of the LIF receptor with Nr1 and gp130 did not increase the affinity of IL-11 binding (FIG. 4B).

Nr1 appears to be a receptor that is specific for IL-11. The binding of $^{125}$I-IL-11 to Ba/F3 cells expressing Nr1 was competed for by unlabelled IL-11, but not IL-6, LIF, OSM or IL-3 (FIG. 5). A more complex situation exists in cells in which Nr1 is expressed with gp130 and the LIF receptor. The binding of $^{125}$I-IL-11 to Ba/F3 cells expressing Nr1 and gp130, was completed for by OSM and unlabelled IL-11 (FIG. 5), while binding to Ba/F3 cells expressing Nr1, gp130 and the LIF receptor was competed for by LIF, as well as OSM and IL-11 (FIG. 5).

EXAMPLE 13

Co-Expression of IL-11 Receptor α-Chain and gp130 Allows a Proliferative and Differentiative Response to IL-11

Many cytokines exert effects upon cell differentiation as well as cell division. In the absence of differentiative stimuli, colonies of parental leukaemic M1 cells are tightly packed and are composed of undifferentiated blast cells. In response to LIF, OSM and IL-6, but not IL-11, M1 colonies grown in semi-solid agar become dispersed because of the induction of macrophage differentiation (FIG. 6). In addition, LIF, OSM and IL-6 suppress the clonogenicity of M1 cells resulting in the development of reduced numbers of colonies. M1 cells expressing the IL-11 receptor α-chain exhibited a normal response to LIF, OSM and IL-6 but now differentiated into macrophages when stimulated by IL-11 (FIG. 6). As with LIF, IL-6 and OSM, fewer colonies were produced by M1 cells expressing Nr1 in the presence of IL-11 than in control cultures and these colonies contained fewer cells.

The IL-3-dependent haemopoietin cell line Ba/F3 has been used to study the capacity of a variety of cytokine receptors to transduce a proliferative signal. Ba/F3 cells are absolutely dependent on IL-3 for proliferation, but do not proliferate in response to IL-11, LIF or IL-6. It was determined, therefore, whether expression of Nr1, gp130 and the LIF receptor broadened the spectrum of cytokines to which these cells could respond. While none of the cell lines examined could proliferate in response to IL-6 alone, each cell line that expressed gp130, irrespective of whether or not other receptors were co-expressed, proliferated in response to a combination of IL-6 and the soluble IL-6 receptor α-chain (FIG. 7). Proliferation in response to LIF required coexpression of the LIF receptor and gp130 (FIG. 7), however, these cells were unable to proliferate in response to IL-11. Likewise, Ba/F3 cells expressing Nr1 alone or Nr1 and the LIF receptor were incapable of responding to IL-11 (FIG. 7). Response to IL-11 required coexpression of both Nr1 and gp130 (FIG. 7). Half-maximal proliferation of these cells occurred at an IL-11 concentration of between 20 and 100 pg/ml. Expression of the LIF receptor, in addition to Nr1 and gp130, did not alter this response (FIG. 7).

EXAMPLE 14

Cloning of the Human IL-11rα

In order to determine the feasibility of cloning the human IL-11rα based on homology with the murine receptor, analy-sis of murine and human genomic DNA was carried out using a murine IL-11rα cDNA fragment as a probe (for method see Example 13). FIG. 10A shows a specific band of 14 kb in human DNA, compared with 4.8 kb in the murine DNA, when examined under conditions of high hybridisation stringency (0.2×SSC, at 65° C.).

The same murine probe (445 bp Sph I/Sac I fragment) was then used to screen approximately $10^6$ plaques from five human cDNA libraries. These included two adult bone marrow libraries (27; Clontech Cat. no. HL1058a) and libraries from the human placenta (Clontech Cat. no. HL1008b), liver (Clontech Cat. no. HL1001a) and a hepatoma cell line (Clontech Cat. no. HL1015b). Positive plaques were isolated and purified by successive rounds of hybridisation-screening (for method see Example 17). Approximately 30 positive clones were obtained from each of the adult bone marrow libraries and the placental library. No positive clones were identified from the liver or hepatoma libraries despite the murine receptor being isolated from this tissue (see previous Examples). The positive plaques were also examined using a PCR-based strategy; plaque eluates were used as templates in a PCR reaction primed with an antisense oligonucleotide encoding the murine WSXWS motif and an appropriate oligonucleotide primer derived from the vector sequence in the region adjacent to the cloning site. Three clones from a bone marrow library were initially chosen for detailed characterisation. Southern analysis using a restriction fragment from the human cDNA identified equivalent bands to those detected using the murine IL-11rα, thus confirming the identity of the human cDNA (FIG. 10B). The nucleotide sequence of the insert from each of these clones (#9.1, #4.3, #8.2), was determined in both directions. The insert from clone #9.1 was used to generate a probe to re-screen the bone marrow cDNA library and resulted in the identification of another unique clone (#17.1, FIG. 11). The nucleotide sequence of this clone was also determined in both directions.

EXAMPLE 15

Sequence Analysis of the Human I-11rα

As depicted in FIG. 11, clones #9.1, and #4.3 were incomplete while clones #8.2 and #17.1 encompassed the entire coding region. Clones #8.2 and #17.1 contained a 287 bp intronic sequence and clones #4.3 and #8.2 contained a 254 bp intronic sequence. These sequences were confirmed as introns by analysis of genomic DNA clones, exhibited typical splice donor-acceptor sequences and were attributed to incomplete splicing of mRNA. FIG. 8 shows the composite nucleotide sequence determined from the four IL-11 rαcDNA clones. The sequence included 127 bp of 5' untranslated region (UTR) that was represented in 3 clones, and a 3' UTR with a polyadenylation signal and poly A tail. There was an open reading frame of 1269 bp which was predicted to encode a protein of 423 amino acids (a.a.). The predicted protein had a potential hydrophobic leader sequence (1-23 a.a.), extracellular region (24-366 a.a.), transmembrane domain (367-392 a.a.) and a cytoplasmic tail (393-423 a.a.). The extracellular domain contained two possible sites of N-linked glycosylation (FIG. 8A-D). As with the murine IL-11rα (see previous Examples) and in common with other cytokine receptors (15;28), the human IL-11rα exhibited an immunoglobulin-like domain and an hemopoietin domain (D200, FIG. 8A-D) in the extracellular region. The latter was composed of two subdomains of 100 a.a. (SD100, FIG. 8) and included proline residues preceding each subdomain, four conserved cysteine residues, a series of polar and hydrophobic residues an the WSXWS motif. The variable amino acid "S" was identified as theonine in the human receptor compared to alanine in the murine equivalent (see previous Examples).

Several differences were noted between clones isolated from the same library. A nucleotide substitution in clone #4.3 (G↔C at 944 bp, FIG. 8A-D) resulted in a different amino acid residue (E↔Q at 273 a.a., FIG. 8). Clone #4.3 and #17.1 differed from clone #8.2 by a nucleotide substitution (G↔A at 1135 bp, FIG. 8A-D) in the coding region with no consequent change in protein. Also, clones #17.1 and #8.2 differed in the 3' UTR by a single substitution (A↔G at 1658 bp, FIG. 8A-D). These differences were interpreted as representing polymorphisms.

Comparison of the sequences of the murine and human IL-11rα chains showed a high degree of homology (FIG. 12). There was overall 85% identity at the nucleic acid level and 84% at the protein level. The homology was more evident in the extracellular and transmembrane regions and less so in the cytoplasmic tail where the human receptor was 8 amino acids shorter than the murine equivalent. Neither protein contained an identifiable tyrosine kinase like domain.

EXAMPLE 16

Expression of the Human IL-11 Receptor α Chain Results in Specific Binding of Human IL-11 and Permits IL-11 Signalling The murine myeloid leukemic cell line M1 (29) constitutively expresses murine gp 130 the signalling molecule for LIF, IL-6, OSM and IL-11 receptors. In response to LIF, OSM and IL-6, colonies of parental M1 cells in semisolid agar become dispersed as cells differentiate into macrophages and acquire the ability to migrate through agar. In addition, there is suppression of clonogenicity leading to reduced colony numbers. M1 cells manipulated to express the murine IL-11rα displayed specific binding of IL-11 and differentiated in response to IL-11 (see previous Examples). The human IL-11rα was expressed in murine M1 cells using the mammalian expression vector pEFBOS (30; Example 15). Binding studies using $^{125}$I-labeled human IL-11 were carried out to test whether IL-11 specifically bound to the these cells (see Example 15 for methods). As shown in Table 3, M1 cells manipuated to express the human IL-11rα (pools #1-#4) demonstrated significant specific binding of human IL-11. The positive control cells, M1 cells and Ba/F3 cells expressing the murine IL-11rα and murine gp130 (see previous Examples) also showed high level binding. As expected, the parental M1 cells exhibited no detectable specific binding of IL-11. Scatchard analysis of saturation isotherms of IL-11 binding to M1 cells that expressed human IL-11rα confirmed high-affinity binding (FIG. 13A-D). The apparent equilibrium dissociation constant ($K_d$) was estimated to be 250 pM. These cells expressed an average 3190 receptors at their surface. This result was comparable to M1 cells expressing murine IL-11rα ($K_d$=275 pM, and 4815 receptors/cell) and was attributed to an interaction of the human IL-11rα with murine gp130.

Table 4 summarises the results of agar culture experiments of M1 cells that expressed human IL-11rα and shows their response to LIF and IL-11. As described above, M1 cells expressing the murine IL-11rα displayed clonal suppression and macrophage differentiation in response to IL-11. In contrast, the central parental M1 cells did not respond to IL-11. The four pools of M1 cells manipulated to express the human IL-11rα when treated with IL-11, showed marked suppression of clonogenicity (Table 4). In addition, the few colonies that grew in IL-11 displayed a differentiated phenotype. All cells lines showed the expected response to LIF.

M1 cells expressing human IL-11rα and control cells were also examined in suspension cultures to assess macrophage differentiation in response to IL-11 and LIF (31; 32). Macrophage morphology was assessed after five days in culture. As shown in FIG. 13A-D, the majority of the cells displayed a macrophage phenotype following stimulation with IL-11. Similar results were observed with M1 cells expressing the murine IL-11rα, while parental M1 cells did not respond to IL-11. Thus, these experiments documented the ability of the isolated human cDNA to encode a functional receptor protein and demonstrated that co-operation between the human IL-11rα and murine gp130 was sufficient for signal transduction.

To directly address the requirement of gp130 to human IL-11 receptor signalling, murine Ba/F3 cells were examined. These cells are totally dependent on IL-3 for survival and do not constitutively express gp130. Ba/F3 cells were manipulated to express human IL-11rα and expanded based on the expression of the co-electroporated puromycin-resistance gene. Three clonal cell lines were established. These were confirmed to express human IL-11rα as assessed by binding of radio-labeled human IL-11, albeit at low level (106; 97; 116; mean specific counts bound per $10^6$ cells versus undetectable binding for parental Ba/F3 cells). As shown in FIG. 14 these cells were unresponsive to IL-11. The human gp130 molecule was then expressed in each of these clonal cell lines:cells then proliferated in response to IL-11 (FIG. 14). This result confirmed the expression of the human IL-11rα in Ba/F3 cells and the requirement for gp130 for proliferation. Parental Ba/F3 cells used as control did not respond to IL-11 and, as expected, all cells proliferated in response to murine IL-3.

EXAMPLE 17

Human Library Screening

The following human cDNA libraries were screened using the above mentioned murine probe:two bone marrow libraries (27; Clontech Cat. no. HL1058a), a placental library (Clontech Cat. no. HL1008b), a liver library (Clontech Cat. no. HL1001a), and a hepatoma cell library (Clontech Cat. no. HL1015b). Approximately $10^6$ plaques from each library were lifted onto nitrocellulose membranes and fixed by incubating at 80° C. for 2 hr. under vacuum. The filters were pre-hybridised for 1 hr. and then hybridised at 65° C. for 16 hr. in a solution containing 2×SSC, 2 mg/ml bovine serum albumin, 2 mg/ml ficoll, 2 mg/ml polyvinylpyrrolidine, 100 μM ATP, 50 μg/ml tRNA, 2 mM sodium pyrophosphate, 2 mg/ml salmon sperm DNA, 200 μg/ml of sodium azide and 1% w/v SDS. The filters were finally washed for 30 mins. at 65° C. with 0.2×SSC, 0.1% SDS. Positive plaques on duplicate filters were isolated and purified by further rounds of hybridisation screening.

Human clone #91. (FIG. 11) was also labeled and used to probe one human bone marrow cDNA library. This resulted in clone #17.1.

An amount of 15 μg of human genomic DNA (obtained from peripheral blood leucocytes) and murine genomic DNA (obtained from the FDCP-1 cell line) was digested to completion with the restriction enzyme Hind III (Boehringer Mannheim, Germany). DNA fragments were separated on an 0.8% w/v agarose gel and transferred with 0.4 M NaOH on to nylon membrane (Gene Screen Plus, Biotechnology Systems, NEN Research Products).

A 445 bp Sph I/Sac I restriction enzyme digest fragment from the murine IL-11rα clone 30.1 (see earlier Examples) and a 560 bp Pst I/Sba I restriction digest fragment from the human cDNA clone #17.1 were used as probes. An amount of 100 ng of DNA was labeled using a random decanucleotide labelling kit (Braesatec, Adelaide, S.A., Australia). The incorporated [$^{32}$P] ATP was separated from unincorporated label using a NICK column (Pharmacia, Uppsala, Sweden). The membrane was prehybridised and hybridised at 65° C. overnight in the buffer recommended by the manufacturer. The membrane was finally washed in 0.1% w/v SDS, 0.2×SSC (30 mM sodium chloride, 3 mM tri-sodium citrate) for 30 min. at 65° C.

EXAMPLE 18

Analysis of Human IL-11rα Positive Plaques

Positive plaques isolated using the murine probe were further screened by a PCR-based strategy. Eluate from pure plaques (5 μl) was used as a template in a 50 μl volume PCR reaction using 2.5 U Taq polymerase (Boehringer Mannheim, Germany), the supplied buffer, 200 μM of each dNTP. The reaction was primed with 250 ng of an anti-sense oligonucleotide primer corresponding to WSXWS motif 5'-[(G/A)CTCCA(N)GC(G/A)CTCAA-3'] (SEQ ID NO. 23) and an appropriate vector oligonucleotide primer that flanked the cloned cDNA:T3 and T7 promoter primers for pBluescript plasmid, and the appropriate γgt10 and γgt11 forward and reverse primers. Control reactions that lacked the template were also performed. Three plaques (#91., #4.3, #8.2 isolated from a bone marrow library) were selected. The cDNA were sequenced on both strands using the dideoxy-termination method (18) and the Pharmacia T7 polymerase sequencing kit (Pharmacia, Uppsala, Sweden).

EXAMPLE 19

Human IL-11rα Expression Constructs and Biological Assays

A composite cDNA construct including the entire coding region and the polyadenylation signal but excluding the intronic sequences was made by ligating restriction enzyme digest fragments from #9.1 (Eco RI/Pst I fragment) and #17.1 (Pst V/Eco RI fragment). The construct was cloned into the Bst XI site of pEF-BOS (30) using Bst XI adaptors (Invitrogen, San Diego, Calif., USA). It was linearized with Aat II prior to electroporation into M1 and Ba/F3 cells. pPGKpuropA and pPGKneopA are pBluescript derivatives containing the cDNA encoding puromycin transferase and neomycin transferase and were co-electroporated into cells and used as a selection markers. Human gp130 cloned into pEF-BOS was electroporated in BaF3 cells manipulated to express the human IL-11rα.

M1 cells (29) were grown in Dulbecco's modified Eagle's medium (DMEM) containing 10% v/v Fetal Calf Serum (FCS) in 10% v/v $CO_2$ at 37° C. Ba/F3 cells (33) were grown in RPMI-1640 medium containing 10% v/v FCS and WEHI-3B D-conditioned media as a source of IL-3 (34). M1 and Ba/F3 cells stably expressing the human IL-11rα construct were generated by electroporation as described above. Cells were co-electroporated with pPGKPuropA. Clones of Ba/F3 expressing human IL-11rα were expanded with puromycin antibiotic selection and human gp130 was introduced with pPGKneopA. These cells were expanded in G418.

For biological assays, M1 cells (300 per ml) were cultured in DMEM, 20% v/v FCS, 0.3% v/v agar and with human IL-11 (1000 U/ml) or murine LIF (1000 U/ml) or normal saline. Cultures were incubated in humidified air with 10% v/v $CO_2$ at 37° C. After 7 days colonies were counted and differentiation was assessed using standard criteria (35). In suspension cultures $1.5 \times 10^4$ M1 cells were cultured in 1.5 ml of DMEM containing 10% v/v FCS and with or without IL-11 (1000 U/ml) or LIF (1000 U/ml) and incubated as above. Differentiation was determined by morphological examination of May-Grunwald Giemsa stained cells: a minimum of 200 cells was examined.

The proliferation of Ba/F3 cells was measured in a microwell assay as described above. Briefly, 200 cells/well were incubated in 15 μl of media containing the following stimuli: normal saline, murine interleukin-3 (IL-3) at final concentration 1000 units/ml and series dilutions of human IL-11. Viable cells were counted after 48 hours.

Iodination of IL-11 using the Bolton-Hunter reagent and binding studies with M1 and Ba/F3 cells were performed as previously described above.

EXAMPLE 20

Source of Cytokines

Murine IL-3 and human IL-11 was purchased from Peprotech (Rocky Hill, N.J., USA) and murine LIF and AMRAD Pty. Ltd. (Melbourne, Australia). Human IL-11 used in ligand binding studies was obtained by expression in COS-M6 cells. Briefly, a cDNA encoding the mature protein for human IL-11 was obtained by polymerase chain reaction from cDNA derived from a human stromal cell line 197/17 (36). The human IL-11 mature coding region was inserted into pEF/IL3SIG/FLAG which is a pEF-BOS (30) derived expression vector containing sequences encoding the murine IL-3 signal sequence followed by the FLAG sequence (Eastman Kodak, CT, USA), and then expressed in COS-M6 cells resulting in the secretion of a biologically active human IL-11 protein with a N-terminal flag. The N-terminal flag human IL-11 was purified by affinity chromatography on an anti-FLAG M2 monoclonal antibody column (Eastman Kodak, CT, USA) as recommended by the manufacturer with peptide elution followed by gel filtration chromatography on Superdex 75 (Pharmacia, Uppsala, Sweden). The purified protein gave a single band of MW 25,000 on SDS polyacrylamide gels.

EXAMPLE 21

Since antibodies to the IL-11 receptor a chain were not available to monitor expression, constructs were engineered to express a soluble version of the murine IL-11 receptor a chain with an N-terminal FLAG epitope (International Biotechnologies/Eastman Kodak, CT, USA). First a derivative of the mammalian expression vector pEF-BOS was generated so that it contained DNA encoding the signal sequence of murine IL-3 (MVLASSTTSIHTMLLLLLMLFHLGLQA-SIS) and the FLAG epitope (DYKDDDDK), followed by a unique Xba I cloning site. This vector was named pEF/IL3SIG/FLAG.

PCR was performed using to amplify DNA fragments encoding the extracellular domain without the transmembrane or cytoplasmic regions (S24 to Q367). The primers used were:

```
                                           (SEQ ID NO:24)
5'-ATCTTCTAGATCCCCTGCCCCCAAGCT-3'

(SEQ ID NO:25)
5' ACTTTCTAGATTATTGCTCCAAGGGGTCCCTGTG-3'
```

The soluble murine IL-11 receptor α chain PCR product was digested with Xba I and cloned, in frame, into the XbaI site of pEF/IL3SIG/FLAG to yield pEF-sIL-11rα.

In order to confirm soluble murine IL-11 receptor α chain could be produced using the expression vectors pEF-SIL-11rα, COS cells were transiently transfected with these constructs. Briefly, COS cells from a confluent 175 cm$^2$ tissue culture flask were resuspended in PBS and electroporated (BioRad Gene pulser; 500 µF, 300 V.) with 20 µg of uncut pEF-sIL-11rα in a 0.4 cm cuvette (BioRad). After 2 to 3 days at 37° C. in a fully humidified incubator containing 10% v/v $CO_2$ in air cells were used for analyses of protein expression. Conditioned medium was collected by centrifugation and stored sterile at 4° C.

Medium was then chromatographed on an anti-FLAG antibody affinity column (International Biotechnologies/Eastman Kodak, CT, USA). Proteins that failed to bind to the column were washed through with PBS containing, while those proteins the murine IL-11 receptor α chain proteins which bound to the column was eluted with 8 ml of ug/ml FLAG peptide. The purified soluble murine IL-11 receptor α chain was electrophoresed on a SDS-polyacrylamide gel, which was stained with silver to reveal the presence of a major band with an apparent molecular weight of approximately 40,000 similar to the predicted size of the soluble murine IL-11 receptor α chain.

The purified soluble murine IL-11 receptor α chain was tested for its ability to stimulate the differentiation of M1 cells in the presence or absence of IL-11. IL-11 and the soluble murine IL-11 receptor α chain were unable to stimulate M1 differentiation alone, however, when combined, differentiation was observed in both liquid and semi-solid culture. These results demonstrate that soluble murine IL-11 receptor α chain may act as an agonist, allowing IL-11 to exert effects on cells expressing gp130 in the absence of membrane bound IL-11 receptor α chain. In this way soluble IL-11 receptor α chain is similar to soluble IL-6 receptor α chain.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

REFERENCES

1. Du, X. X. and Williams, D. A. (1994) *Blood* 83: 2023-2030.
2. Yang, Y. C. and Yin, T. (1992) *Biofactors* 4: 15-21.
3. Paul, S. R., Bennett, F., Calvetti, J. A., Kelleher, K., Wood, C. R., O'Hara, R. J. J., Leary, A. C., Sibley, B., Clark, S. C., Williams, D. A. and Yang, Y.-C. (1990) *Proc. Natl. Acad. Sci. USA* 87: 7512.
4. Musashi, M., Clark, S. C., Sudo, T., Urdal, D. L., and Ogawa, M. (1991) *Blood* 78: 1448-1451.
5. Schibler, K. R., Yang, Y. C. and Christensen, R. D. (1992) *Blood* 80: 900-3.
6. Tsuji, K., Lyman, S. D., Sudo, T., Clark, S. C., and Ogawa, M. (1992) *Blood* 79: 2855-60.
7. Burstein, S. A., Mei, R. L., Henthorn, J., Friese, P. and turner, K. (1992) *J. Cell. Physiol.* 153: 305-12.
8. Hangoc, G., Yin, T., Cooper, S., Schendel, P., Yang, Y. C. and Broxmeyer, H. E. (1993) *Blood* 81: 965-72.
9. Teramura, M., Kobayashi, S., Hoshino, S., Oshimi, K. and Mizoguchi, H. (1992) *Blood* 79: 327-31.
10. Yonemura, Y., Kawakita, M., Masuda, T., Fujimoto, K., Kato, K. and Takatsuki, K. (1992) *Exp. Hematol.* 20: 1011-6.
11. Baumann, H. and Schendel, P. (1991) *J. Biol. Chem.* 266: 20424-7.
12. Kawashima, I., Ohsumi, J., Mita-Honjo, K., Shimoda-Takano, K., Ishikawa, H., Sakakibara, S., Miyadai, K. and Takiguchi, Y. (1991) *Febs. Lett.* 283: 199-202.
13. Keller, D. C., Du, X. X., Srour, E. f., Hoffman, R. and Williams, D. A. (1993) *Blood* 82: 1428-35.
14. Yin, T., Miyazawa, K. and Yang, Y. C. (1992) *J. Biol. Chem.* 267: 8347-51.
15. Bazan, J. F. (1990) *Proc. Natl. Acad. Sci. USA* 87: 6934-8.
16. Cosman, D., Lyman, S. D. Idzerda, R. L., Beckmann, M. P., Park, L. S., Goodwin, R. G. and March, C. J. (1990) *Trends Biochem. Sci.* 15: 265-70.
17. Gearing, D. P., King, J. A., Gough, N. M., and Nicola, N. A. (1989) *EMBO J.* 8: 3667-76.
18. Sanger, F. A., Nicken, J. and Coulson, A. R. (1977) *Proc. Natl. Acad. Sci. USA* 74: 5463-5467.
19. Reed, K. C. and Mann, D. A. (1987) *Nucl. Acids Res.* 13: 7207-7221.
20. Gough, N. M. (1988) *Anal. Biochem.* 173: 93-95.
21. Gonda, T., et al. (1982) *Mol. Cell. Biol.* 2: 617-624.
22. Chomczynski, P. and Sacchi, N. (1987) *Anal. Biochem.* 162: 156-159.
23. Hilton, D. J. and Nicola, N. A. (1992) *J. Biol. Chem.* 267: 10238-47.
24. Bolton, A. E. and Hunter, W. M. (1973) *Biochem. J.* 133: 529-539.
25. Gearing, D. P., Nicola, N. A., Metcalf, D., Foote, S., Willson, T. A., Gough, N. M. and Williams, L. (1989) *BioTechnology* 7: 1157-61.
26. Sambrook, J., Fritsch, E. F. and Maniatis, T. (1989) *Molecular cloning: A Laboratory Manual* Cold Spring Harbor Laboratory, Cold Spring Harbor, N.Y.
27. Begley, C. G., Aplan, P. D., Denning, S. M., Haynes, B. F., Waldmann, T. A. & Kirsch, I. R. (1989). *Proc. Natl. Acad. Sci. USA*, 86, 10128-10132.
28. (Tetsuga & Kishimoto, 1992)
29. Ichikawa, Y. (1969). *J. Cell. Physiol.*, 74, 223-234.
30. Mizushima, S. & Nagata, S. (1990). *Nucl. Acid. Res.*, 18, 5322.
31. Tanigawa, T., Elwood, N., Metcalf, D., Cary, D., DeLuca, E., Nicola, N., and Begley, G. C. (1993). *Proc. Natl. Acad. Sci. USA*, 90, 7864-7868.
32. Tanigawa, T., Nicola, N., McArthur, G., Strasser, A., and Begley, C. G. (1995). *Blood*, 85, 379-390.
33. Palacios, R. and Steinmetz, M. (1985) *Cell*, 41, 727-734.
34. Metcalf, D. (1984) *Haemopoietic Colony Stimulating Factors*. Elsevier, Amsterdam.
35. Metcalf, D., (1985). *Science*, 229, 16-22.
36. Novotny, J. R., Dyehrsen, U., Welch, K., Layton, J. E., Cebon, J. S., and Boyd, A. W. (1990). *Exp Hematol*, 18, 775-784.

The invention claimed is:

1. An isolated nucleic acid encoding an IL-11 receptor α chain which comprises the amino acid sequence having at least 95% identity with SEQ ID NO: 5, wherein said amino acid sequence comprises Trp-Ser-Xaa-Trp-Ser (SEQ ID NO: 1) and wherein said IL-11 receptor α a chain binds to IL-11.

2. An isolated nucleic acid encoding an IL-11 receptor α a chain which comprises Trp-Ser-Xaa-Trp-Ser (SEQ ID NO: 1), wherein said nucleic acid comprises the nucleotide sequence that hybridizes to the complement of SEQ ID NO: 4 under high stringency conditions comprising hybridization at 65° C and washing in 0.2X SSC, 0.1% w/v SDS at 65° C. and wherein said IL-11 receptor α chain binds to IL-11.

3. A recombinant vector comprising the nucleic acid according to claim 1 or 2.

* * * * *